United States Patent
Strickley et al.

(10) Patent No.: US 12,370,200 B2
(45) Date of Patent: Jul. 29, 2025

(54) PHARMACEUTICAL COMPOSITION CONTAINING BREXANOLONE, GANAXOLONE, OR ZURANOLONE, AND USE THEREOF

(71) Applicant: Brii Biosciences, Inc., Durham, NC (US)

(72) Inventors: Robert G. Strickley, Durham, NC (US); Lianhong Xu, Durham, NC (US); Zhi Hong, Durham, NC (US)

(73) Assignee: Brii Biosciences, Inc., Durham, NC (US)

( * ) Notice: Subject to any disclaimer, the term of this patent is extended or adjusted under 35 U.S.C. 154(b) by 889 days.

(21) Appl. No.: 17/610,236

(22) PCT Filed: May 8, 2020

(86) PCT No.: PCT/US2020/032172
§ 371 (c)(1),
(2) Date: Nov. 10, 2021

(87) PCT Pub. No.: WO2020/231837
PCT Pub. Date: Nov. 19, 2020

(65) Prior Publication Data
US 2022/0241295 A1   Aug. 4, 2022

Related U.S. Application Data

(60) Provisional application No. 63/018,815, filed on May 1, 2020, provisional application No. 62/846,576, filed on May 10, 2019.

(51) Int. Cl.
*A61K 31/568*   (2006.01)
*A61K 9/14*   (2006.01)
(Continued)

(52) U.S. Cl.
CPC ........... *A61K 31/568* (2013.01); *A61K 9/145* (2013.01); *A61K 31/57* (2013.01); *A61K 31/573* (2013.01); *A61K 31/575* (2013.01); *A61K 31/58* (2013.01)

(58) Field of Classification Search
CPC .... A61K 31/568; A61K 31/57; A61K 31/573; A61K 31/575; A61K 9/0019; A61K 9/10
See application file for complete search history.

(56) References Cited

U.S. PATENT DOCUMENTS 3,174,970 A   3/1965   Georges et al.
3,574,198 A   4/1971   Radscheit et al.
(Continued)

FOREIGN PATENT DOCUMENTS

CN   107106574 A   8/2017
GB   1409239 A   10/1975
(Continued)

OTHER PUBLICATIONS

Andreen et al., Psychoneuroendocrinology (2009) 34, 1121-1132 (Year: 2009).*
(Continued)

*Primary Examiner* — San Ming R Hui
(74) *Attorney, Agent, or Firm* — Cooley LLP

(57) ABSTRACT

Disclosed herein is a pharmaceutical composition comprising a pharmaceutically effective amount of a neuroactive steroid that is a positive modulator of γ aminobutyric acid type A ($GABA_A$) receptors. Also disclosed are methods of treating diseases using the pharmaceutical composition and processes of producing the pharmaceutical composition.

37 Claims, 8 Drawing Sheets

(51) Int. Cl.
   A61K 31/57    (2006.01)
   A61K 31/573   (2006.01)
   A61K 31/575   (2006.01)
   A61K 31/58    (2006.01)

(56) References Cited

U.S. PATENT DOCUMENTS

| | | | |
|---|---|---|---|
| 9,029,355 | B2 | 5/2015 | Shaw et al. |
| 9,452,176 | B2 | 9/2016 | Shaw et al. |
| 9,512,165 | B2 | 12/2016 | Martinez Botella et al. |
| 9,777,037 | B2 | 10/2017 | Gravanis et al. |
| 10,172,870 | B2 | 1/2019 | Reddy |
| 10,251,894 | B2 | 4/2019 | Rogawski et al. |
| 10,711,030 | B2 | 7/2020 | Torregrossa et al. |
| 11,266,663 | B2 | 3/2022 | Pinna et al. |
| 2016/0228454 | A1 | 8/2016 | Zhang et al. |
| 2018/0071315 | A1 | 3/2018 | Cashman et al. |
| 2018/0296487 | A1 | 10/2018 | Saporito et al. |
| 2018/0340005 | A1 | 11/2018 | Marx et al. |
| 2019/0117673 | A1 | 4/2019 | Shaw et al. |
| 2020/0377547 | A1 | 12/2020 | Salituro et al. |
| 2023/0118577 | A1 | 4/2023 | Xu et al. |
| 2024/0009121 | A1 | 1/2024 | Hong et al. |

FOREIGN PATENT DOCUMENTS

| | | | | |
|---|---|---|---|---|
| JP | S4867263 | A | | 9/1973 |
| WO | WO-2013112605 | A2 | | 8/2013 |
| WO | WO-2014169833 | A1 | | 10/2014 |
| WO | WO-2016040322 | A1 | | 3/2016 |
| WO | WO-2016127170 | A1 | | 8/2016 |
| WO | WO-2017066626 | A1 | * | 4/2017 ............. A61K 31/57 |
| WO | WO-2017156103 | A1 | | 9/2017 |
| WO | WO-2018013613 | A1 | | 1/2018 |
| WO | WO-2018103626 | A1 | | 6/2018 |
| WO | WO-2018195186 | A1 | | 10/2018 |
| WO | WO-2020118142 | A1 | | 6/2020 |
| WO | WO-2020206462 | A1 | | 10/2020 |
| WO | WO-2020231837 | A1 | | 11/2020 |
| WO | WO-2020243488 | A1 | | 12/2020 |
| WO | WO-2021142477 | A1 | | 7/2021 |
| WO | WO-2021174205 | A1 | | 9/2021 |
| WO | WO-2022040216 | A9 | | 4/2022 |

OTHER PUBLICATIONS

Brittain, H.G., et al. "Polymorphism in pharmaceutical solids" edited by H. G. Brittain, Marcel Dekker, D.J.W., Grant (chapter 1), p. 1-10 and J. K. Guillory (chapter 5); p. 183-226 (1999).
Byrn, S., et al., "Pharmaceutical solids: a strategic approach to regulatory considerations", Pharmaceutical Research (1995); 12(7): 945-954.
Kharkevich, D.A., "Pharmacology", 8th ed. M.: GEOTAR-Media, 2005; 3 pages.
Dyson, G., et al., "Chemistry of Synthetic Drugs", Moscow, MIR, 1964, pp. 12-19; 25 pages, with English machine translation.
Hirayama, Y., "Handbook for organic compound crystal—Principle and know-how," 2008, 28 pages.
Hoag et al., "Chapter 2: Particle and Power Bed Properties", Pharmaceutical Dosage Forms: Tablets 3rd edition, Jun. 3, 2008, 58 pages.
Knigochey "Popular Medical Encyclopedia", editor-in-chief V.I. Pokrovsky, 4th ed., St, 1997, 2 pages.
Notice of Reasons for Refusal for Japanese Application No. JP20210566976 mailed Jun. 5, 2024, with English translation, 8 Pages.
Office Action and Search Report for Russian Application No. RU2022121496 mailed Jun. 7, 2024, with English translation, 23 pages.
Office Action and Search Report for Taiwan Application No. TW112103512 mailed Sep. 12, 2024, with English translation, 7 pages.
Office Action for Indian Patent Application No. IN202117056325 dated Apr. 19, 2024, with English translation, 6 pages.
Office Action for Israel Application No. 287905 mailed Jul. 17, 2024, 7 pages.
Office Action for Mexican Application No. MX/a/2021/013695 mailed Jul. 11, 2024, with partial English translation, 10 pages.
Office Action for Russian Application No. RU2021136231 dated Apr. 9, 2024, 16 pages.
Office Action for the Mexican Application No. MX/a/2022/008614 dated Apr. 2, 2024, with partial English translation, 15 pages.
Search Report and Written Opinion for Singapore Application No. 11202251136H mailed Sep. 9, 2024, 12 pages.
Extended European Search Report for European Application No. EP20210738878 dated Jan. 30, 2024, 15 pages.
Lewbart "Synthesis of the four pairs of side-chain epoxides epimeric at C-20 derived from 5. beta.-pregnan-3. alpha.-ol". The Journal of Organic Chemistry. May 1968; 33(5): 1695-706.
Office Action for Chinese Patent Application No. CN202080042380.9 dated Mar. 7, 2024, 12 pages.
Gunduz-Bruce, H. et al., "Trial of SAGE-217 in patients with major depressive disorder," The New England Journal of Medicine, Sep. 2019, 381(10), pp. 903-911.
Harrison et al., "Alphaxalone selectively potentiates responses to GABA and muscimol in rat cuneate nucleus in vitro," Journal of the Physiology-London, Jan. 1984, vol. 346, p. 42-p. 42.
Majewska et al., "Steroid Hormone Metabolites Are Barbiturate-Like Modulators of the GABA Receptor," Science, 232, May 1986, pp. 1004-1007, PubMed: 2422758.
Zorumski et al., "Neurosteroids, stress and depression: Potential therapeutic opportunities," Neuroscience and Biobehavioral Reviews, Jan. 2013, 37(1), pp. 109-122, DOI: 10.1016/j.neubiorev.2012.10.005.
Office Action for Chinese Patent Application No. CN202080042380.9 dated Oct. 24, 2024, with English translation, 8 pages.
Beck, CT, "Revision of the Postpartum Depression Predictors Inventory," Journal of Obstetric, Gynecologic & Neonatal Nursing, Jul. 2002, 31(4), pp. 394-402.
Cox JL, et al., "A controlled study of the onset, duration and prevalence of postnatal depression," British Journal of Psychiatry, Jul. 1993, 163, pp. 27-31.
Extended European Search Report for European Application No. EP20200805552 dated Apr. 11, 2023, 7 pages.
Fisher SD, et al., "Four maternal characteristics determine the 12-month course of chronic severe postpartum depressive symptoms," Depress Anxiety, Apr. 2019, 36(4), pp. 375-383. https://doi.org/10.1002/da.22879.
Hoffmann E., "Brexanolone Injection Administration to Lactating Women: Breast Milk Allopregnanolone Levels [30J]," Obstetrics & Gynecology, vol. 133, No. 5 Supplement, May 2019, 115S, 1 page.
Hoffmann, et al., "Evaluation of breast milk concentrations following brexanolone iv administration to healthy lactating woman," American Journal of Obstetrics & Gynecology, S554 Supplement to Jan. 2019, 1 page.
International Preliminary Report on Patentability for International Application No. PCT/US2021/046347, mailed Mar. 2, 2023, 9 pages.
McEvoy et al., "Neuroactive Steroids and Perinatal Depression: a Review of Recent Literature," Current Psychiatry Reports, 20:78, Sep. 2018, pp. 1-9, https://doi.org/10.1007/s 11920-018-0937-4.
Moreira, MWL et al., "Postpartum depression prediction through pregnancy data analysis for emotion-aware smart systems," Information Fusion, May 2019, vol. 47, pp. 23-31, doi: 10.1016/j.inffus.2018.07.001.
Munk-Olsen, "Population-Based Assessment of the Recurrence Risk of Postpartum Mental Disorders: Will It Happen Again?," JAMA Psychiatry, 77(2), pp. 213-214, Feb. 2020 (2019 online), doi: 10.1001/jamapsychiatry.2019.3208.
Schiller, et al., "Allopregnanolone as a mediator of affective switching in reproductive mood disorders," Psychopharmacology, 231(17), pp. 3557-3567, Sep. 2014, doi: 10.1007/s00213-014-3599-x.

(56) References Cited

OTHER PUBLICATIONS

Werner, et al., "Preventing postpartum depression: review and recommendations," Archives of Women's Mental Health, 18(1), Feb. 2015 (ePub 2014), pp. 41-60, doi: 10.1007/s00737-014-0475-y 2014.

Caira "Crystalline Polymorphism of Organic Compounds", Topics in Current Chemistry (Jan. 1, 1998); 198:163-208.

Morissette et al., "High-Throughput Crystallization: Polymorphs, Salts, Co-Crystals and Solvates of Pharmaceutical Solids," Advanced Drug Delivery Reviews, vol. 56, No. 3, Feb. 2004, pp. 275-300.

Office Action and Search Report for Russian Application No. RU2021136231 dated Oct. 12, 2023, 22 pages.

Pertsev "Pharmaceutical and Medico-biological Aspects of Drugs", Kharkiv, UkrFA Publishing House (1999); 1: 253-254; 7 pages.

Smirnova et al., Clinical pharmacokinetics: theoretical, applied and analytical aspects: a guide / Ed. V.G. Kukes. (Chapter 11.2. Relationship of the Crystal Structure of a Substance, Pharmacokinetics and Effectiveness of a Drug, 2009, 22 pages.

Chen, W. et al., "Effect of Particle Size on Drug Loading and Release Kinetics of Gefitinib-Loaded PLGA Microspheres" Mol. Pharmaceutics, Dec. 14, 2016, vol. 14, No. 2, pp. 459-467.

Hoshyar, N. et al., "The effect of nanoparticle size on in vivo pharmacokinetics and cellular interaction" Nanomedicine, Mar. 22, 2016, vol. 11, No. 6, pp. 673-692.

Office Action and Search Report for Chinese Application No. CN202080042380.9 dated Jul. 18, 2023, 23 pages.

Office Action for Singapore Application No. SG11202112111W mailed Aug. 4, 2023, 12 pages.

International Search Report and Written Opinion for Application No. PCT/US2020/023172, mailed Jul. 31, 2020, 9 pages.

International Search Report and Written Opinion for Application No. PCT/US2021/046347, mailed Dec. 8, 2021, 12 pages.

International Search Report and Written Opinion for International Application No. PCT/US2021/013112, mailed Apr. 13, 2021, 8 pages.

Irwin et al., "Allopregnanolone Preclinical Acute Pharmacokinetic and Pharmacodynamic Studies to Predict Tolerability and Efficacy for Alzheimer's Disease," Plos One, vol. 10, No. 6, Jun. 3, 2015, p. e0128313, 31 pages, XP055562355.

Kanes et al., "Open-label, proof-of-concept study of brexanolone in the treatment of severe postpartum depression," Human Psychopharmacology, Clinical and Experimental., vol. 32, No. 2, Mar. 1, 2017 (Mar. 1, 2017), pp. e2576, 6 pages, XP055745579.

Ligsay et al., "A randomized double-blind, placebo-controlled trial of ganaxolone in children and adolescents with fragile X syndrome," Journal of Neurodevelopmental Disorders, 9:26, Dec. 2017, 13 pages.

Mares et al., "Anticonvulsant action of allopregnanolone in immature rats," Epilepsy Research, Elsevier Science Publishers, Amsterdam, NL, vol. 70, No. 2-3, Aug. 1, 2006 (Aug. 1, 2006), pp. 110-117, XP027974309.

Metcalf et al. "Indices of ovulation: Comparison of Plasma and Salivary Levels of Progesterone with Urinary Pregnanediol", J. Endocr. 1984. vol. 100, pp. 75-80.

Office Action and Search Report for Taiwan Application No. 109115629, mailed Sep. 14, 2021, 17 pages.

PubChem-CID-57390981, Modify Date: Apr. 23, 2022 (Apr. 23, 2022), p. 2.

PubChem-SID-275053753, Modify Date: Nov. 21, 2016 (Nov. 21, 2016), p. 2, Fig.

Rasmusson et al., "A randomized controlled trial of ganaxolone in posttraumatic stress disorder," Psychopharmacology, 234:2245-2257, Aug. 2017.

Hartmann et al., Synthesis and Evaluation of Aliphatic Heterocycle-substituted Steroidal Inhibitors of Alpha-hydroxylase/c17-20-lyase (P450 17). Journal of medicinal chemistry. Nov. 16, 2000;43(23):4437-45.

Kabat "A novel route to 2-fluoromethyl-and 2-hydroxymethyl-4-alkyl furans via allene oxides". Tetrahedron letters. Oct. 7, 1996;37(41):7437-40.

Li et al., "Synthesis and evaluation of pregnane derivatives as inhibitors of human testicular 17α-hydroxylase/C17, 20-lyase". Journal of medicinal chemistry. Oct. 11, 1996;39(21):4335-9.

Office Action for Australian Application No. 2020275291 mailed Dec. 19, 2024, 5 pages.

Office Action for European Application No. 20805552.5 mailed Feb. 19, 2025, 4 pages.

Office Action for Japanese Application No. 2022-542380 mailed Mar. 3, 2025, with English Translation, 6 pages.

Office Action for Mexican Application No. MX/a/2021/013695 mailed Feb. 25, 2025, with English translation, 11 pages.

Office Action for Mexican Application No. MX/a/2021/013695 mailed Nov. 28, 2024, with English translation, 12 pages.

Office Action for Russian Application No. 2021136231 mailed Dec. 2, 2024, with English translation, 25 pages.

Office Action for Russian Application No. 2022121496 mailed Dec. 19, 2024, with English translation, 12 pages.

Office Action for Taiwan Application No. 110130362, mailed Feb. 19, 2025, with partial English translation, 8 pages.

* cited by examiner

| # | Solvent | TC | RC | EV | Water Activity |
|---|---|---|---|---|---|
| 1 | Water | ✓ | | | 1.00 |
| 2 | Methanol | ✓ | ✓ | ✓ | |
| 3 | 2-Methoxyethanol | | | ✓ | |
| 4 | 1-Propanol | | | ✓ | |
| 5 | Nitromethane | ✓ | ✓ | | |
| 6 | Acetonitrile | ✓ | | | |
| 7 | Dimethylsulfoxide | | | ✓ | |
| 8 | Acetone | ✓ | | | |
| 9 | 2-Butanone | | ✓ | ✓ | |
| 10 | Dichloromethane | | ✓ | ✓ | |
| 11 | Methyl acetate | ✓ | ✓ | ✓ | |
| 12 | 4-Methyl-2-pentanone | ✓ | ✓ | ✓ | |
| 13 | Chloroform | | | ▨ | |
| 14 | Ethyl acetate | ✓ | ✓ | ✓ | |
| 15 | Chlorobenzene | ✓ | ✓ | ✓ | |
| 16 | Tetrahydrofuran | | ✓ | ✓ | |
| 17 | 1,4-Dioxane | | | ✓ | |
| 18 | Isopropyl ether | ✓ | | | |
| 19 | Toluene | ✓ | ✓ | ✓ | |
| 20 | Cyclohexane | ✓ | | | |
| 21 | Heptane | ✓ | | | |
| 22 | 1-Butanol | | | | |
| 23 | 2-Propanol | ✓ | ✓ | ✓ | |
| 24 | Trifluoroethanol | | | ✓ | |
| 25 | Dimethyl carbonate | ✓ | ✓ | | |

FIG. 4

| # | Solvent | | | | | |
|---|---|---|---|---|---|---|
| 26 | t-Butyl methyl ether | | | ■ | | |
| 27 | Isopropyl acetate | ■ | ■ | ■ | | |
| 28 | Ethanol | | | ■ | | |
| 29 | 1-Methoxy-2-propanol | | | ■ | | |
| 30 | Cyclohexanone | | | | | |
| 31 | N,N-Dimethylformamide | | | ■ | | |
| 32 | 2-Methoxyethyl ether | | | | | |
| 33 | Methanol: Water (95:5) | ■ | | | | 0.20 |
| 34 | Acetonitrile: Water (95:5) | ■ | | | | 0.60 |
| 35 | Acetone: Water (95:5) | ■ | | | | 0.63 |
| 36 | Tetrahydrofuran: Water (95:5) | | | ■ | | 0.88 |
| 37 | 2-propanol: Water (95:5) | | | | | 0.54 |
| 38 | Methanol: Water (90:10) | ■ | | ■ | | 0.33 |
| 39 | Acetonitrile: Water (90:10) | ■ | | | | 0.76 |
| 40 | Acetone: Water (90:10) | ■ | | ■ | | 0.77 |
| 41 | Tetrahydrofuran: Water (90:10) | | | ■ | | 0.94 |
| 42 | 1,4-Dioxane: Water (90:10) | ■ | | ■ | | 0.69 |
| 43 | 2-propanol: Water (90:10) | ■ | ■ | ■ | | 0.76 |
| 44 | Acetone: Water (80:20) | ■ | | | | 0.86 |
| 45 | Ethanol: Water (20:80) | ■ | | | | 0.95 |
| 46 | 2-Propanol: Dimethylsulfoxide (80:20) | | | ■ | | |
| 47 | Acetonitrile: Dimethylsulfoxide (80:20) | ■ | | | | |
| 48 | N-Methyl-2-pyrrolidone | | | | | |

FIG. 4 CONT.

PHARMACEUTICAL COMPOSITION CONTAINING BREXANOLONE, GANAXOLONE, OR ZURANOLONE, AND USE THEREOF

CROSS-REFERENCE

This application is a U.S. National Phase of International Application No. PCT/US2020/032172, filed on May 8, 2020, which claims the benefit of U.S. Provisional Application No. 62/846,576, filed May 10, 2019, and U.S. Provisional Application No. 63/018,815, filed May 1, 2020, each of which is incorporated herein by reference in its entirety.

FIELD OF DISCLOSURE

The present disclosure is related to a pharmaceutical composition comprising brexanolone, ganaxolone, zuranolone (SAGE-217) or a combination thereof for treating diseases such as epilepsy-related, depression and other central nervous system disorders.

BACKGROUND OF DISCLOSURE

A number of endogenous and synthetic compounds, such as neuroactive steroids and derivatives, can impact central nervous system (CNS) function through multiple mechanism, include but not limited to, positive allosteric modulation of $GABA_A$ ($\gamma$ aminobutyric acid type A) receptors that is related to many central nervous system disorders. Allopregnanolone is one of such neuroactive steroids that have short terminal half-lives and poor oral bioavailability, and have limited clinical use as oral therapies or parenteral therapy. Brexanolone is a synthetic compound that is chemically identical to endogenous allopregnanolone. Ganaxolone, another such neuroactive steroids and a synthetic pregnane steroid, has a relatively long half-life, approximately 20 hours in human plasma after oral administration and a short maximum concentration ($T_{max}$) (US Patent Application Publication No.: 20160228454). Both ganaxolone and brexanolone can modulate activities of $GABA_A$ receptors (PCT Patent Publications WO2017156103A1, WO2016127170A1, U.S. Pat. Nos. 9,029,355, 9,452,176, 10,172,870).

Brexanolone intravenous injection product (brexanolone IV, ZULRESSO™, developed and under trademark of Sage Therapeutics, Cambridge, MA, USA) was recently approved by US Food and Drug Administration (FDA, March 2019) for the treatment of postpartum depression (PPD), a serious and potentially life-threatening condition, for which no current pharmacotherapies are specifically indicated. However, ZULRESSO™ is inconvenient to use and is administered to a patient by continuous intravenous (IV) infusion that lasts for a total of about 60 hours (2.5 days).

Ganaxolone is currently under clinical trials for treating severe postpartum depression (PPD) and pediatric epilepsy with efficacy successes (Marinus Pharmaceuticals). Both intravenous injection and oral formulations of ganaxolone are being developed and tested (US Patent Publication No.: 20160228454A1; Clinical Trial ID: NCT03228394, MAGNOLIA trial; Ligsay, et al., Journal of Neurodevelopmental Disorders, 9:26, 2017; Rasmusson, et al., Psychopharmacology, 234:2245-2257, 2017, DOI 10.1007/s00213-017-4649-y). However, effects of these formulations are still to be optimized.

New and improved formulations are therefore needed for enhanced bioavailability, long lasting effect, and/or fast and convenient delivery.

SUMMARY OF THE INVENTION

In one aspect, disclosed here is a pharmaceutical composition comprising a pharmaceutically effective amount of a neuroactive steroid, wherein the neuroactive steroid is a positive modulator of gamma-aminobutyric acid type A ($GABA_A$) receptor; and wherein plasma concentration of the neuroactive steroid reaches a maximum plasma concentration ($C_{max}$) in about 30 minutes to 6 hours and maintains the plasma concentration of more than about 5% of the $C_{max}$ for at least about 5 days, after a single dose of the pharmaceutical composition is administered by intramuscular or subcutaneous injection.

Also disclosed is a pharmaceutical composition comprising particles comprising at least one neuroactive steroid and one or more pharmaceutical acceptable excipients, the neuroactive steroid being a positive modulator of $\gamma$ aminobutyric acid type A ($GABA_A$) receptors; wherein, the particles comprise large particles having a particle size in a range of from about 1.5 µm to about 15 µm and small particles having a particle size in a range of from about 0.2 µm to about 1.5 µm; and wherein, about 0.01% to about 50% of the particles are small particles and about 50% to 99.99% of the particles are large particles, percentage based on the total weight of the particles. The neuroactive steroid can be a positive modulator of $GABA_A$ receptors and can comprise tetrahydrodeoxycorticosterone (THDOC), androstane, androstane 3α-androstanediol, cholestane cholesterol, pregnane, pregnane pregnanolone (eltanolone), allopregnanolone, brexanolone, ganaxolone, zuranolone (SAGE-217) or a combination thereof.

In another aspect, disclosed here is a process for producing a pharmaceutical composition comprising particles, the process comprising: a) producing a particle mixture comprising neuroactive steroid selected from brexanolone, ganaxolone, zuranolone (SAGE-217) or a combination thereof and one or more pharmaceutical acceptable excipients; b) milling a first portion of the particle mixture to produce a large particle mixture, wherein at least 50% of the large particle mixture are large particles having a particle size in a range of from about 1.5 µm to about 15 µm, percentage based on the total weight of the particle mixture; and c) producing a pharmaceutical composition comprising the particles comprising about 50% to 99.99% of the large particles, percentage based on the total weight of the particles.

In another aspect, disclosed here is a method for treating a disease in a subject in need thereof, the method comprising administering a subject a pharmaceutical composition disclosed here or a pharmaceutical composition produced by a process disclosed here. The pharmaceutical composition can be administered to the subject via intramuscular (IM) injection, subcutaneous (SC) injection, intravenous (IV) injection or a combination thereof.

Also disclosed is a method of treating a disease in a subject in need thereof can comprise: administering a pharmaceutical composition comprising a pharmaceutically effective amount of a neuroactive steroid to the subject by intramuscular or subcutaneous injection with a single dose in a range of from 0.5 to 10 mg per kilogram of body weight of the subject, wherein the neuroactive steroid is a positive modulator of gamma-aminobutyric acid type A ($GABA_A$) receptor; and wherein plasma concentration of the neuroactive steroid reaches a maximum plasma concentration ($C_{max}$) in about 30 minutes to 6 hours and maintains the plasma concentration of more than about 5% of the $C_{max}$ for at least about 5 days in the subject, after he pharmaceutical composition is administered to the subject by intramuscular or subcutaneous injection.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF DRAWING

FIG. 1A: a pharmaceutical composition comprises minimum amounts, such as less than 1% of small particles and mostly large particles. FIG. 1B: A pharmaceutical composition comprises some small particles and mostly large particles. FIG. 1C: A pharmaceutical composition comprises increasing amounts of small particles and large particles. FIG. 1D: A pharmaceutical composition comprises comparable amounts of small particles and large particles. D50=mass-median-diameter (MMD), wherein 50% of particles are below and 50% of particles are above a given diameter. Mean Large=mean particle size of the large particles. Mean Small=mean particle size of the small particles.

FIG. 2A: Brexanolone structure. FIG. 2B: Small brexanolone particle size distribution. FIG. 2C: Large brexanolone particle size distribution. FIG. 2D-FIG. 2E: Pharmacokinetics (PK) in rats showing rat plasma brexanolone concentrations over time after administration. Legend: Open diamond, brexanolone suspension of small particle, 25 mg/kg; Open square, brexanolone suspension of large particles, 25 mg/kg; Solid square, IV solution (Comparative) 1 mg/kg; and Solid triangle, IM solution (Comparative) 12.5 mg/kg.

FIG. 3A: Ganaxolone structure. FIG. 3B: Distribution of 4.1 µm ganaxolone particles. FIG. 3C: Distribution of 3.6 µm ganaxolone particles. FIG. 3D-FIG. 3E: Pharmacokinetics (PK) in rats showing rat plasma concentrations over time after administration. Legend: Open diamond, ganaxolone suspension of 1 µm particles, 25 mg/kg; Open square, ganaxolone suspension of 4 µm particles, 25 mg/kg; Solid square, IV solution (Comparative); and Solid diamond, IM solution (Comparative).

FIG. 4. Summary of crystal-form screen results under three conditions: 1) Temperature-cycled ripening of brexanolone slurries between 40-5° C. for two days (TC) (n=48); 2) Heating slurries to 40° C. followed by hot filtration, then storing of brexanolone solutions at 4° C. for up to two days (RC) (n=48); 3) Evaporation of brexanolone solutions at ambient conditions for up to 7 days (EV) (n=48).

DETAILED DESCRIPTION

Figure 1A:
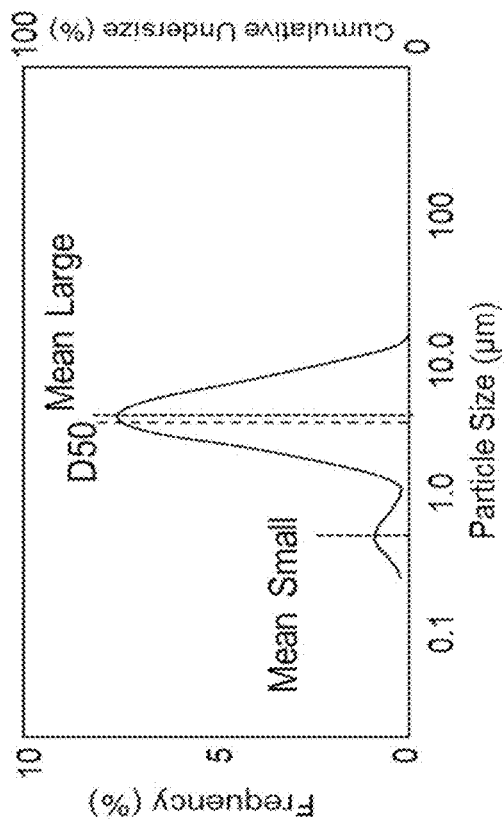
FIG. 1A-FIG. 1D. Schematic illustrations of exemplary particle size distributions.

The features and advantages of the disclosed compositions and methods will be more readily understood, by those of ordinary skill in the art, from reading the following detailed description. It is to be appreciated that certain features of the disclosed compositions and methods, which are, for clarity, described above and below in the context of separate embodiments, may also be provided in combination in a single embodiment. Conversely, various features of the disclosed compositions and methods that are, for brevity, described in the context of a single embodiment, may also be provided separately or in any sub-combination. In addition, references in the singular may also include the plural (for example, "a" and "an" may refer to one, or one or more) unless the context specifically states otherwise.

The use of numerical values in the various ranges specified in this application, unless expressly indicated otherwise, are stated as approximations as though the minimum and maximum values within the stated ranges were both proceeded by the word "about." In this manner, slight variations above and below the stated ranges can be used to achieve substantially the same results as values within the ranges. Also, the disclosure of these ranges is intended as a continuous range including every value between the minimum and maximum values.

The term "about" and its grammatical equivalents in relation to a reference numerical value and its grammatical equivalents as used herein can include a range of values plus or minus 10% from that value, such as a range of values plus or minus 10%, 9%, 8%, 7%, 6%, 5%, 4%, 3%, 2%, or 1% from that value. For example, the amount "about 10" includes amounts from 9 to 11.

As used herein, the term "γ aminobutyric acid type A receptors", "gamma-aminobutyric acid type A receptors", "gamma-aminobutyric acid A receptors", "$GABA_A$ receptors", "$GABA_ARs$", "$GABA_AR$" or a grammatic variation thereof, either in singular or in plural form, refers to gamma-aminobutyric acid type A receptors ($GABA_ARs$) that are a class of receptors that respond to the neurotransmitter gamma-aminobutyric acid (GABA). GABA is the principal inhibitory neurotransmitter in the cerebral cortex that is important for maintaining the inhibitory state that counterbalances neuronal excitation. Disorder in $GABA_A$ receptors or imbalance of GABA and neuroexcitation can lead to seizures and other central nervous system disfunctions. A number of natural and synthetic neuroactive steroids can bind to $GABA_ARs$ and modulate their activities.

The term "neuroactive steroid", "neuroactive steroids" or a grammatical variation thereof refers to one or more neurosteroids that exert inhibitory actions on neurotransmission, specifically, on the $GABA_A$ receptors. Examples of neurosteroids can include, but not limited, tetrahydrodeoxycorticosterone (THDOC), androstane, androstane 3α-androstanediol, cholestane cholesterol, pregnane, pregnane pregnanolone (eltanolone), allopregnanolone, brexanolone, ganaxolone and zuranolone (SAGE-217).

The term "particles" or grammatical variations thereof can refer to particles disclosed herein and, in examples, can also refer to stabilized particles that are stable under physiological conditions without changing its physical or chemical form for an extended period of time, such as for a time period in a range of from 0.1 to 20 hours, 1 to 50 hours, 2 to 75 hours, 5 to 100 hours, 1 to 5 days, 2 to 7 days, 3 to 10 days, 4 to 20 days, or longer.

The terms D10, D50 and D90 are commonly used to represent the midpoint and range of the particle sizes of a given sample. The term "D10" refers to 10% of particles are below and 90% of particles are above a defined measurement, for example a particle diameter. The term "D50" refers to a mass-median-diameter (MMD), wherein 50% of particles are below and 50% of particles are above a defined measurement, for example a particle diameter. The term "D90" refers to 90% of particles are below and 10% of particles are above a defined measurement, for example a particle diameter. In examples, D50=1.5 µm means 50% of particles are below 1.5 µm and 50% of particle are above 1.5 µm. In further examples, D90=4.0 µm means 90% particles are below 4.0 µm in diameter and 10% of particles are above 4.0 µm in diameter. The percentage can be based on total volume of particles, total weight of particles, total number of particles or a total area of the particles measured. In examples, a sample of particles are measured by light scattering with about $1\times10^6$ particles measured. A measurement data of D50=0.9 µm means about 50% of particles measured are below 0.9 µm and 50% are above 0.9 µm, percentage based on the total number of particles measured. In further examples, particle sizes are measured using microscopy and imaging technology or optical granulometry techniques, wherein particles in certain fields are measured. With this, a percentage can be the total number of particles measured or a given area measured.

The term "particle size" refers to a primary particle size or crystallite size that is the smallest particle size. When particles of primary size aggregate together, the aggregate can have an aggregate particle size that is typically a multiple of the primary particle size. The particle size used herein refers to the largest dimension of a primary particle, for example, a diameter of a spherical particle, a longest length of a rod or bar shaped particle, or a largest size measured across an irregular shaped particle.

The term "mean particle size" refers to an average of particle sizes of the particles measured or selected.

The term "$C_{max}$", "Cmax" or "maximum plasma concentration" refers to the maximum (or peak) plasma concentration that a drug reaches in a specified compartment or part of the body after the drug has been administered and before the administration of a second dose.

Pharmaceutical Composition

The disclosed pharmaceutical composition can comprise a pharmaceutically effective amount of a neuroactive steroid, wherein the neuroactive steroid is a positive modulator of gamma-aminobutyric acid type A ($GABA_A$) receptor; and wherein the neuroactive steroid reaches a maximum plasma concentration ($C_{max}$) in about 10 minutes to 6 hours and maintains a plasma concentration of more than about 5% of the $C_{max}$ for at least about 1 day, after a single dose of the pharmaceutical composition by intramuscular or subcutaneous injection.

The pharmaceutical composition can comprise a pharmaceutically effective amount of a neuroactive steroid, wherein the amount of neuroactive steroid which can be combined with a carrier material to produce a single dosage form can vary depending upon the subject being treated and the particular mode of administration and can generally be that amount of the pharmaceutical composition which produces a therapeutic effect. Generally, the amount of neuroactive steroid can range from about 0.01% to about 99% (w/w) of the composition, for example, can be about 0.1%-1%, about 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, or 95%-99% of the pharmaceutical composition. Preferably, the amount of neuroactive steroid can be from about 0.1% to about 70%, and most preferably from about 1% to about 30% of the pharmaceutical composition.

The pharmaceutical composition can comprise a pharmaceutically effective amount of a neuroactive steroid, wherein the neuroactive steroid is a positive modulator of gamma-aminobutyric acid type A ($GABA_A$) receptor; wherein the neuroactive steroid reaches a maximum plasma concentration ($C_{max}$) in a subject in about 10 minutes to 6 hours and maintains a plasma concentration of the neuroactive steroid in the subject more than about 5% of the $C_{max}$ for at least about 1 day, after a single dose of the pharmaceutical composition is administered to the subject by intravenous (IV) injection, intramuscular (IM) injection, subcutaneous (SC) injection or a combination thereof; and wherein the maximum plasma concentration ($C_{max}$) is measured from one or more specimens from the subject.

In some cases, the Cmax can be reached in about 10 minutes to about 360 minutes. In some cases, the Cmax can be reached in about 10 minutes to about 20 minutes, about 10 minutes to about 30 minutes, about 10 minutes to about 40 minutes, about 10 minutes to about 50 minutes, about 10 minutes to about 60 minutes, about 10 minutes to about 120 minutes, about 10 minutes to about 180 minutes, about 10 minutes to about 240 minutes, about 10 minutes to about 300 minutes, about 10 minutes to about 360 minutes, about 20 minutes to about 30 minutes, about 20 minutes to about 40 minutes, about 20 minutes to about 50 minutes, about 20 minutes to about 60 minutes, about 20 minutes to about 120 minutes, about 20 minutes to about 180 minutes, about 20 minutes to about 240 minutes, about 20 minutes to about 300 minutes, about 20 minutes to about 360 minutes, about 30 minutes to about 40 minutes, about 30 minutes to about 50 minutes, about 30 minutes to about 60 minutes, about 30 minutes to about 120 minutes, about 30 minutes to about 180 minutes, about 30 minutes to about 240 minutes, about 30 minutes to about 300 minutes, about 30 minutes to about 360 minutes, about 40 minutes to about 50 minutes, about 40 minutes to about 60 minutes, about 40 minutes to about 120 minutes, about 40 minutes to about 180 minutes, about 40 minutes to about 240 minutes, about 40 minutes to about 300 minutes, about 40 minutes to about 360 minutes, about 50 minutes to about 60 minutes, about 50 minutes to about 120 minutes, about 50 minutes to about 180 minutes, about 50 minutes to about 240 minutes, about 50 minutes to about 300 minutes, about 50 minutes to about 360 minutes, about 60 minutes to about 120 minutes, about 60 minutes to about 180 minutes, about 60 minutes to about 240 minutes, about 60 minutes to about 300 minutes, about 60 minutes to about 360 minutes, about 120 minutes to about 180 minutes, about 120 minutes to about 240 minutes, about 120 minutes to about 300 minutes, about 120 minutes to about 360 minutes, about 180 minutes to about 240 minutes, about 180 minutes to about 300 minutes, about 180 minutes to about 360 minutes, about 240 minutes to about 300 minutes, about 240 minutes to about 360 minutes, or about 300 minutes to about 360 minutes. In some cases, the Cmax can be reached in about 10 minutes, about 20 minutes, about 30 minutes, about 40 minutes, about 50 minutes, about 60 minutes, about 120 minutes, about 180 minutes, about 240 minutes, about 300 minutes, or about 360 minutes.

In some cases, the neuroactive steroid can maintain a plasma concentration in the subject at a level more than about 5% of the Cmax for about 1 day to about 100 days. In some cases, the neuroactive steroid can maintain a plasma concentration in the subject at a level more than about 5% of the $C_{max}$ for at least about 1 day. In some cases, the neuroactive steroid can maintain a plasma concentration in the subject at a level more than about 5% of the $C_{max}$ for at most about 100 days. In some cases, the neuroactive steroid can maintain a plasma concentration in the subject at a level more than about 5% of the $C_{max}$ for about 1 day to about 5 days, about 1 day to about 10 days, about 1 day to about 20 days, about 1 day to about 30 days, about 1 day to about 50 days, about 1 day to about 100 days, about 5 days to about 10 days, about 5 days to about 20 days, about 5 days to about 30 days, about 5 days to about 50 days, about 5 days to about 100 days, about 10 days to about 20 days, about 10 days to about 30 days, about 10 days to about 50 days, about 10 days to about 100 days, about 20 days to about 30 days, about 20 days to about 50 days, about 20 days to about 100 days, about 30 days to about 50 days, about 30 days to about 100 days, or about 50 days to about 100 days. In some cases, the neuroactive steroid can maintain a plasma concentration in the subject at a level more than about 5% of the $C_{max}$ for about 1 day, about 5 days, about 10 days, about 20 days, about 30 days, about 50 days, or about 100 days.

In some cases, a single dose of the disclosed pharmaceutical composition can be about 0.5 mg to about 50 mg per kilogram (kg) of body weight. In some cases, a single dose can be at least about 0.5 mg per kg of body weight. In some cases, a single dose can be at most about 50 mg per kg of body weight. In some cases, a single dose can be about 0.5 mg to about 2 mg per kg of body weight, about 0.5 mg to about 4 mg per kg of body weight, about 0.5 mg to about 6 mg per kg of body weight, about 0.5 mg to about 8 mg per kg of body weight, about 0.5 mg to about 10 mg per kg of body weight, about 0.5 mg to about 20 mg per kg of body weight, about 0.5 mg to about 50 mg per kg of body weight, about 2 mg to about 4 mg per kg of body weight, about 2 mg to about 6 mg per kg of body weight, about 2 mg to about 8 mg per kg of body weight, about 2 mg to about 10 mg per kg of body weight, about 2 mg to about 20 mg per kg of body weight, about 2 mg to about 50 mg per kg of body weight, about 4 mg to about 6 mg per kg of body weight, about 4 mg to about 8 mg per kg of body weight, about 4 mg to about 10 mg per kg of body weight, about 4 mg to about 20 mg per kg of body weight, about 4 mg to about 50 mg per kg of body weight, about 6 mg to about 8 mg per kg of body weight, about 6 mg to about 10 mg per kg of body weight, about 6 mg to about 20 mg per kg of body weight, about 6 mg to about 50 mg per kg of body weight, about 8 mg to about 10 mg per kg of body weight, about 8 mg to about 20 mg per kg of body weight, about 8 mg to about 50 mg per kg of body weight, about 10 mg to about 20 mg per kg of body weight, about 10 mg to about 50 mg per kg of body weight, or about 20 mg to about 50 mg per kg of body weight. In some cases, a single dose can be about 0.5 mg per kg of body weight, about 2 mg per kg of body weight, about 4 mg per kg of body weight, about 6 mg per kg of body weight, about 8 mg per kg of body weight, about 10 mg per kg of body weight, about 20 mg per kg of body weight, or about 50 mg per kg of body weight. In a particular example, the single dose can be about 3.5 mg to 5 mg per kg of body weight. The body weight refers to the body weight of a subject, such as a human patient or an animal subject.

In some cases, a unit dose of the disclosed pharmaceutical composition can be about 50 mg to about 800 mg. In some cases, a single unit dose can be at least about 50 mg. In some cases, a single unit dose can be at most about 800 mg. In some cases, a single unit dose can be about 50 mg to about 100 mg, about 50 mg to about 200 mg, about 50 mg to about 300 mg, about 50 mg to about 400 mg, about 50 mg to about 600 mg, about 50 mg to about 800 mg, about 100 mg to about 200 mg, about 100 mg to about 300 mg, about 100 mg to about 400 mg, about 100 mg to about 600 mg, about 100 mg to about 800 mg, about 200 mg to about 300 mg, about 200 mg to about 400 mg, about 200 mg to about 600 mg, about 200 mg to about 800 mg, about 300 mg to about 400 mg, about 300 mg to about 600 mg, about 300 mg to about 800 mg, about 400 mg to about 600 mg, about 400 mg to about 800 mg, or about 600 mg to about 800 mg. In some cases, a single unit dose can be about 50 mg, about 100 mg, about 200 mg, about 300 mg, about 400 mg, about 600 mg, or about 800 mg. A unit dose is form of package of the pharmaceutical composition that can be administered to a subject in a single dose. For example, a 300 mg unit dose of a pharmaceutical composition can be packaged in a certain volume, such as one milliliter volume, in an injectable form that can be injected into a subject in a single injection. In other examples, a 300 mg of a pharmaceutical composition can be packaged in a certain number of tablets, such as one tablet, that can be administered to a subject in one oral dose. In yet other examples, a 300 mg unit dose of a pharmaceutical composition can be packaged in a certain volume, such as 0.5 milliliter volume, in an injectable form that can be injected into a subject in a single subcutaneous injection.

In some cases, a single dose of the disclosed pharmaceutical composition can be about 50 mg to about 800 mg. In some cases, a single dose can be at least about 50 mg. In some cases, a single dose can be at most about 800 mg. In some cases, a single dose can be about 50 mg to about 100 mg, about 50 mg to about 200 mg, about 50 mg to about 300 mg, about 50 mg to about 400 mg, about 50 mg to about 600 mg, about 50 mg to about 800 mg, about 100 mg to about 200 mg, about 100 mg to about 300 mg, about 100 mg to about 400 mg, about 100 mg to about 600 mg, about 100 mg to about 800 mg, about 200 mg to about 300 mg, about 200 mg to about 400 mg, about 200 mg to about 600 mg, about 200 mg to about 800 mg, about 300 mg to about 400 mg, about 300 mg to about 600 mg, about 300 mg to about 800 mg, about 400 mg to about 600 mg, about 400 mg to about 800 mg, or about 600 mg to about 800 mg. In some cases, a single dose can be about 50 mg, about 100 mg, about 200 mg, about 300 mg, about 400 mg, about 600 mg, or about 800 mg.

A single dose can be adjusted when using a unit dose to administer the pharmaceutical composition to a subject based on the body weight of the subject. In one example, a unit dose of 300 mg in 1 mL injectable solution is designed for a single dose injection to a subject of body weight in a range of from 60 kg to 70 kg. For a subject having body weight less than 60 kg, an adjusted dose, such as 0.5 mL of the 300 mg unit dose, can be injected to the subject in one injection. For a subject having body weight more than 70 kg, an adjusted dose, such as 1.5 mL of the 300 mg unit dose, can be injected to the subject in one injection. The single dose can be adjusted to have the required mg of the pharmaceutical composition per kilogram (kg) of body weight as disclosed herein.

The single dose of the disclosed pharmaceutical composition can be in a range of from about 0.5 to 50 mg per kilogram (kg) of body weight and/or can be produced by combining one or more unit doses, or a part thereof, wherein each of the unit doses can be in a range of from 50 mg to 800 mg per unit dose. The ranges of single dose, unit dose or a combination thereof disclosed above and hereafter are suitable and are incorporated as examples.

In some cases, the disclosed pharmaceutical composition can have a neuroactive steroid concentration of about 5 mg/mL to about 800 mg/mL. In some cases, the neuroactive steroid concentration can be at least about 5 mg/mL. In some cases, the neuroactive steroid concentration can be at most about 800 mg/mL. In some cases, the neuroactive steroid concentration can be about 5 mg/mL to about 10 mg/mL, about 5 mg/mL to about 50 mg/mL, about 5 mg/mL to about 100 mg/mL, about 5 mg/mL to about 200 mg/mL, about 5 mg/mL to about 400 mg/mL, about 5 mg/mL to about 800 mg/mL, about 10 mg/mL to about 50 mg/mL, about 10 mg/mL to about 100 mg/mL, about 10 mg/mL to about 200 mg/mL, about 10 mg/mL to about 400 mg/mL, about 10 mg/mL to about 800 mg/mL, about 50 mg/mL to about 100 mg/mL, about 50 mg/mL to about 200 mg/mL, about 50 mg/mL to about 400 mg/mL, about 50 mg/mL to about 800 mg/mL, about 100 mg/mL to about 200 mg/mL, about 100 mg/mL to about 400 mg/mL, about 100 mg/mL to about 800 mg/mL, about 200 mg/mL to about 400 mg/mL, about 200 mg/mL to about 800 mg/mL, or about 400 mg/mL to about 800 mg/mL. In some cases, the neuroactive steroid concentration can be about 5 mg/mL, about 10 mg/mL, about 50 mg/mL, about 100 mg/mL, about 200 mg/mL, about 400 mg/mL, or about 800 mg/mL.

In some cases, the neuroactive steroid can maintain a plasma concentration of more than about 10%, 15%, 20%, 25%, or 30% of the $C_{max}$ for at least about 10, 20, 30, 40, 50, or 60 days. The neuroactive steroid can maintain a plasma concentration of more than about 10% the $C_{max}$ for at least about 10 days in one example, 15% the $C_{max}$ for at least about 10 days in another example, 20% the $C_{max}$ for at least about 10 days in yet another example, 25% the $C_{max}$ for at least about 10 days in yet another example, 35% the $C_{max}$ for at least about 10 days in yet another example, 10% the $C_{max}$ for at least about 20 days in another example, 15% the $C_{max}$ for at least about 20 days in another example, 25% the $C_{max}$ for at least about 20 days in yet another example, 35% the $C_{max}$ for at least about 20 days in yet another example, 10% the $C_{max}$ for at least about 30 days in another example, 15% the $C_{max}$ for at least about 30 days in another example, 25% the $C_{max}$ for at least about 30 days in yet another example, 35% the $C_{max}$ for at least about 30 days in yet another example, 10% the $C_{max}$ for at least about 40 days in another example, 15% the $C_{max}$ for at least about 40 days in another example, 25% the $C_{max}$ for at least about 40 days in yet another example, 35% the $C_{max}$ for at least about 40 days in yet another example, 10% the $C_{max}$ for at least about 50 days in another example, 15% the $C_{max}$ for at least about 50 days in another example, 25% the $C_{max}$ for at least about 50 days in yet another example, 35% the $C_{max}$ for at least about 50 days in yet another example, 10% the $C_{max}$ for at least about 60 days in another example, 15% the $C_{max}$ for at least about 60 days in another example, 25% the $C_{max}$ for at least about 60 days in yet another example, 35% the $C_{max}$ for at least about 60 days in yet another example, 10% the $C_{max}$ for at least about 60 or more days in another example, 15% the $C_{max}$ for at least about 60 or more days in another example, 25% the $C_{max}$ for at least about 60 or more days in yet another example or 35% the $C_{max}$ for at least about 60 or more days in yet another example. In one particular example, the neuroactive steroid can maintain a plasma concentration of more than about 15% of the $C_{max}$ for at least about 30 days.

In some cases, the $C_{max}$ can be about 1 ng/mL to about 100 ng/mL. In some cases, the $C_{max}$ can be at least about 1 ng/mL. In some cases, the $C_{max}$ can be at most about 100 ng/mL. In some cases, the $C_{max}$ can be about 1 ng/mL to about 10 ng/mL, about 1 ng/mL to about 20 ng/mL, about 1 ng/mL to about 40 ng/mL, about 1 ng/mL to about 60 ng/mL, about 1 ng/mL to about 80 ng/mL, about 1 ng/mL to about 100 ng/mL, about 10 ng/mL to about 20 ng/mL, about 10 ng/mL to about 40 ng/mL, about 10 ng/mL to about 60 ng/mL, about 10 ng/mL to about 80 ng/mL, about 10 ng/mL to about 100 ng/mL, about 20 ng/mL to about 40 ng/mL, about 20 ng/mL to about 60 ng/mL, about 20 ng/mL to about 80 ng/mL, about 20 ng/mL to about 100 ng/mL, about 40 ng/mL to about 60 ng/mL, about 40 ng/mL to about 80 ng/mL, about 40 ng/mL to about 100 ng/mL, about 60 ng/mL to about 80 ng/mL, about 60 ng/mL to about 100 ng/mL, or about 80 ng/mL to about 100 ng/mL. In some cases, the $C_{max}$ can be about 1 ng/mL, about 10 ng/mL, about 20 ng/mL, about 40 ng/mL, about 60 ng/mL, about 80 ng/mL, or about 100 ng/mL. In particular examples, the $C_{max}$ is in a range of from 20 to 90 ng/mL.

In some cases, the single dose can be in a range of from 3 to about 5 mg per kilogram of body weight, and/or the neuroactive steroid can maintain a plasma concentration of more than about 10 ng/mL for at least about 5 days. In particular examples, the neuroactive steroid can maintain a plasma concentration of more than 10, 20, 25, 30, 40, 50, 60, 70, 80, 90, 100 ng/mL for at least about 10, 20, 30, 40, 50, or 60 days. In some cases, the neuroactive steroid can maintain a plasma concentration of more than 10 ng/mL for at least about 10 days in one example, more than 20 ng/mL for at least about 10 days in another example, more than 30 ng/mL for at least about 10 days in yet another example, more than 40 ng/mL for at least about 10 days in yet another example, more than 50 ng/mL for at least about 10 days in yet another example, more than 60 ng/mL for at least about 10 days in yet another example, more than 70 ng/mL for at least about 10 days in yet another example, more than 80 ng/mL for at least about 10 days in yet another example, more than 90 ng/mL for at least about 10 days in yet another example, more than 100 ng/mL for at least about 10 days in yet another example, more than 10 ng/mL for at least about 20 days in one example, more than 20 ng/mL for at least about 20 days in another example, more than 30 ng/mL for at least about 20 days in yet another example, more than 40 ng/mL for at least about 20 days in yet another example, more than 50 ng/mL for at least about 20 days in yet another example, more than 60 ng/mL for at least about 20 days in yet another example, more than 70 ng/mL for at least about 20 days in yet another example, more than 80 ng/mL for at least about 20 days in yet another example, more than 90 ng/mL for at least about 20 days in yet another example, more than 100 ng/mL for at least about 20 days in yet another example, more than 10 ng/mL for at least about 30 days in one example, more than 20 ng/mL for at least about 30 days in another example, more than 30 ng/mL for at least about 30 days in yet another example, more than 40 ng/mL for at least about 30 days in yet another example, more than 50 ng/mL for at least about 30 days in yet another example, more than 60 ng/mL for at least about 30 days in yet another example, more than 70 ng/mL for at least about 30 days in yet another example, more than 80 ng/mL for at least about 30 days in yet another example, more than 90 ng/mL for at least about 30 days in yet another example, more than 100 ng/mL for at least about 30 days in yet another example, more than 10 ng/mL for at least about 40 days in one example, more than 20 ng/mL for at least about 40 days in another example, more than 30 ng/mL for at least about 40 days in yet another example, more than 40 ng/mL for at least about 40 days in yet another example, more than 50 ng/mL for at least about 40 days in yet another example, more than 60 ng/mL for at least about 40 days in yet another example, more than 70 ng/mL for at least about 40 days in yet another example, more than 80 ng/mL for at least about 40 days in yet another example, more than 90 ng/mL for at least about 40 days in yet another example, more than 100 ng/mL for at least about 40 days in yet another example, more than 10 ng/mL for at least about 50 days in one example, more than 20 ng/mL for at least about 50 days in another example, more than 30 ng/mL for at least about 50 days in yet another example, more than 40 ng/mL for at least about 50 days in yet another example, more than 50 ng/mL for at least about 50 days in yet another example, more than 60 ng/mL for at least about 50 days in yet another example, more than 70 ng/mL for at least about 50 days in yet another example, more than 80 ng/mL for at least about 50 days in yet another example, more than 90 ng/mL for at least about 50 days in yet another example, more than 100 ng/mL for at least about 50 days in yet another example, more than 10 ng/mL for at least about 60 days in one example, more than 20 ng/mL for at least about 60 days in another example, more than 30 ng/mL for at least about 60 days in yet another example, more than 40 ng/mL for at least about 60 days in yet another example, more than 50 ng/mL for at least about 60 days in yet another example, more than 60 ng/mL for at least about 60 days in yet another example, more than 70 ng/mL for at least about 60 days in yet another example, more than 80 ng/mL for at least about 60 days in yet another example, more than 90 ng/mL for at least about 60 days in yet another example, more than 100 ng/mL for at least about 60 days in yet another example, more than 10 ng/mL for at least about 60 or more days in one example, more than 20 ng/mL for at least about 60 or more days in another example, more than 30 ng/mL for at least about 60 or more days in yet another example, more than 40 ng/mL for at least about 60 or more days in yet another example, more than 50 ng/mL for at least about 60 or more days in yet another example, more than 60 ng/mL for at least about 60 or more days in yet another example, more than 70 ng/mL for at least about 60 or more days in yet another example, more than 80 ng/mL for at least about 60 or more days in yet another example, more than 90 ng/mL for at least about 60 or more days in yet another example and more than 100 ng/mL for at least about 60 or more days in yet another example. In one further example, the neuroactive steroid can maintain a plasma concentration of more than 20 ng/mL for at least about 30 days.

In some cases, the pharmaceutical composition releases less than about 5%-50% of the neuroactive steroid within about 1 hour of the single dose of the pharmaceutical composition by intramuscular or subcutaneous injection. Particularly, the pharmaceutical composition can release less than about 5%-50% in one example, 10%-50% in another example, 15%-50% in yet another example, 20%-50% in yet another example, 25%-50% in yet another example, 30%-50% in yet another example, 40%-50% in yet another example and 45%-50% in yet another example, of the neuroactive steroid into plasma of a subject within about 1 hour of the single dose of the pharmaceutical composition administered to the subject by intramuscular or subcutaneous injection. The percentage of release is based on measured plasma concentration of the neuroactive steroid and the total amount of the neuroactive steroid in the single dose of the pharmaceutical composition administered to the subject.

In some cases, the pharmaceutical composition can have a relative bioavailability (Bioavailability$_{IM/SC}$/Bioavailability$_{IV}$) of about 2%-50% at 24 hours after the single dose by intramuscular or subcutaneous injection, in comparison to the same dose by intravenous administration. In some cases, the relative bioavailability can be about 2% to about 50%. In some cases, the relative bioavailability can be at least about 2%. In some cases, the relative bioavailability can be at most about 50%. In some cases, the relative bioavailability can be about 2% to about 5%, about 2% to about 10%, about 2% to about 20%, about 2% to about 30%, about 2% to about 40%, about 2% to about 50%, about 5% to about 10%, about 5% to about 20%, about 5% to about 30%, about 5% to about 40%, about 5% to about 50%, about 10% to about 20%, about 10% to about 30%, about 10% to about 40%, about 10% to about 50%, about 20% to about 30%, about 20% to about 40%, about 20% to about 50%, about 30% to about 40%, about 30% to about 50%, or about 40% to about 50%. In some cases, the relative bioavailability can be about 2%, about 5%, about 10%, about 20%, about 30%, about 40%, or about 50%.

In some cases, the disclosed pharmaceutical composition can comprise particles comprising at least one neuroactive steroid and one or more pharmaceutical acceptable excipients, wherein the neuroactive steroid is a positive modulator of γ aminobutyric acid type A (GABA$_A$) receptors; wherein, particles comprise large particles having a particle size in a range of from about 1.5 µm to about 15 µm and small particles having a particle size in a range of from about 0.2 µm to about 1.5 µm; and wherein, about 0.01% to about 50% of the particles are small particles and about 50% to 99.99% of the particles are large particles, percentage based on the total weight of the particles. In any of embodiments or examples of the pharmaceutical composition, the particles can be stabilized particles disclosed herein.

In some cases, the disclosed pharmaceutical composition can comprise a pharmaceutically effective amount of a neuroactive steroid, wherein the neuroactive steroid is a positive modulator of gamma-aminobutyric acid type A (GABA$_A$) receptor; wherein the neuroactive steroid reaches a maximum plasma concentration (C$_{max}$) in a subject in about 30 minutes to 6 hours and maintains a plasma concentration of the neuroactive steroid more than about 5% of the C$_{max}$ for at least about 5 days, after a single dose of the pharmaceutical composition is administered to the subject by intravenous (IV) injection, intramuscular (IM) injection, subcutaneous (SC) injection or a combination thereof; wherein, the pharmaceutical composition comprising particles of the neuroactive steroid; wherein, the particles comprise large particles having a particle size in a range of from about 1.5 µm to about 15 µm and small particles having a particle size in a range of from about 0.2 µm to about 1.5 µm; and wherein, about 0.01% to about 50% of the particles are small particles and about 50% to 99.99% of the particles are large particles, percentage based on the total weight of the particles.

In some cases, the maximum plasma concentration (C$_{max}$) is measured from specimens from the subject.

In some cases, the particles can have a D50 in a range of from 1.2 µm to about 6.0 µm. The D50 can be 1.2 µm in one example, 1.3 µm in another example, 1.4 µm in yet another example, 1.5 µm in yet another example, 1.6 µm in yet another example, 1.7 µm in yet another example, 1.8 µm in yet another example, 1.9 µm in yet another example, 2.0 µm in yet another example, 2.2 µm in yet another example, 2.4 µm in yet another example, 2.6 µm in yet another example, 2.8 µm in yet another example, 3.0 µm in yet another example, 3.5 µm in yet another example, 4.0 µm in yet another example, 4.5 µm in yet another example, 5.0 µm in yet another example, 5.5 µm in yet another example, 6.0 µm in yet another example, or any one value in the range of from 1.2 µm through 6.0 µm in a further example.

The neuroactive steroid of the disclosed pharmaceutical composition can comprise tetrahydrodeoxycorticosterone (THDOC), androstane, androstane 3α-androstanediol, cholestane cholesterol, pregnane, pregnane pregnanolone (eltanolone), allopregnanolone, brexanolone, ganaxolone, zuranolone (SAGE-217) or a combination thereof. For example, the neuroactive steroid can be brexanolone.

In some cases, the large particles can have a mean particle size in a range of from 2.0 to 6.0 µm in one example, a mean particle size in a range of from 3.0 to 5.0 µm in another example, a mean particle size in a range of from 0.4 to 1.3 µm in yet another example and a mean particle size in a range of from 0.5 to 0.9 µm in a further example.

The pharmaceutical composition can further comprise one or more pharmaceutical acceptable excipients. The pharmaceutical acceptable excipients can comprise surfactant, emulsifier, filler, carrier, isotonicfier, dispersing agent, viscosity modifier, resuspending agent, buffer or a combination thereof. Pharmaceutical excipients typically do not have properties of a medicinal or drug active ingredient, also known as active pharmaceutical ingredient (API) and are typically used to streamline the manufacture process or packaging of the active ingredients, or to deliver an API to a patient or other subject. Pharmaceutical acceptable excipients or inactive ingredients from the Inactive Ingredients Database available from US FDA (https://www.fda.gov/drugs/drug-approvals-and-databases/inactive-ingredients-database-download) can be suitable. Some of Generally Recognized As Safe (GRAS) food substances available form US FDA's GRAS Substances (SCOGS) Database (https://www.fda.gov/food/generally-recognized-safe-gras/gras-substances-scogs-database) can also be suitable.

In some cases, the pharmaceutical acceptable excipients can comprise acacia, animal oils, benzyl alcohol, benzyl benzoate, calcium stearate, carbomers, cetostearyl alcohol, cetyl alcohol, cholesterol, cyclodextrins, dextrose, diethanolamine, emulsifying wax, ethylene glycol palmitostearate, glycerin, glycerin monostearate, glycerol stearate, glyceryl monooleate, glyceryl monostearate, hydrous, histidine, hydrochloric acid, hydroxypropyl cellulose, hydroxypropyl-β-cyclodextrin (HPBCD), hypromellose (hydroxypropyl methylcellulose (HPMC)), lanolin, lanolin alcohols, lecithin, medium-chain triglycerides, metallic soaps, methylcellulose, mineral oil, monobasic sodium phosphate, monoethanolamine, oleic acid, polyyethylene glycols (PEG 3350, PEG 4000, PEG 6000), polyoxyethylene-polyoxypropylene copolymer (poloxamer), polyoxyethylene alkyl ethers, polyoxyethylene castor oil, polyoxyethylene castor oil derivatives, polyoxyethylene sorbitan fatty acid esters, polyoxyethylene stearates, polysorbate, polyoxyethylene (20) sorbitan monolaurate (Tween 20, Polysorbate 20), polyoxyethylene (20) sorbitan monooleate (Tween 80, Polysorbate 80), povidone, propylene glycol alginate, saline, sodium chloride, sodium citrate, sodium citrate dihydrate, sodium hydroxide, sodium lauryl sulfate, sodium phosphate monobasic, sodium phosphate dibasic, sorbitan esters, stearic acid, stearyl alcohol, sunflower oil, tragacanth, triethanolamine, vegetable oils, water, xanthan gum, or a combinations thereof.

In some cases, the pharmaceutical acceptable excipients can comprise dextrose, glycerin, histidine, hydrochloric acid, hydroxypropyl cellulose, hydroxypropyl-β-cyclodextrin (HPBCD), hypromellose (hydroxypropyl methylcellulose (HPMC)), polyoxyethylene (20) sorbitan monolaurate (Tween 20, Polysorbate 20), polyyethylene glycols (PEG 3350, PEG 4000, PEG 6000), polyoxyethylene-polyoxypropylene copolymer (Poloxamer 188, Poloxamer 407), polyoxyethylene (20) sorbitan monooleate (Tween 80, Polysorbate 80), saline, sodium chloride, sodium citrate, sodium citrate dihydrate, sodium lauryl sulfate, sodium phosphate monobasic, sodium phosphate dibasic, or a combination thereof.

The pharmaceutical composition can be suitable for intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, the pharmaceutical composition can be administered via a non-parenteral route, such as a topical, epidermal or mucosal route of administration, e.g., intranasally, orally, vaginally, rectally, sublingually or topically. The pharmaceutical composition can be in the form of sterile aqueous solutions or dispersions. The pharmaceutical composition can also be formulated in a microemulsion, liposome, or other ordered structure suitable to high drug concentration.

The pharmaceutical composition can comprise a population of particles comprising the neuroactive steroid, wherein the particles have a mean particle size of about 0.1-50 µm. In some cases, the particles can have a mean particle size of about 0.1 µm to about 50 µm. In some cases, the particles can have a mean particle size of at least about 0.1 µm. In some cases, the particles can have a mean particle size of at most about 50 µm. In some cases, the particles can have a mean particle size of about 0.1 µm to about 0.2 µm, about 0.1 µm to about 0.5 µm, about 0.1 µm to about 1 µm, about 0.1 µm to about 2 µm, about 0.1 µm to about 5 µm, about 0.1 µm to about 10 µm, about 0.1 µm to about 20 µm, about 0.1 µm to about 30 µm, about 0.1 µm to about 40 µm, about 0.1 µm to about 50 µm, about 0.2 µm to about 0.5 µm, about 0.2 µm to about 1 µm, about 0.2 µm to about 2 µm, about 0.2 µm to about 5 µm, about 0.2 µm to about 10 µm, about 0.2 µm to about 20 µm, about 0.2 µm to about 30 µm, about 0.2 µm to about 40 µm, about 0.2 µm to about 50 µm, about 0.5 µm to about 1 µm, about 0.5 µm to about 2 µm, about 0.5 µm to about 5 µm, about 0.5 µm to about 10 µm, about 0.5 µm to about 20 µm, about 0.5 µm to about 30 µm, about 0.5 µm to about 40 µm, about 0.5 µm to about 50 µm, about 1 µm to about 2 µm, about 1 µm to about 5 µm, about 1 µm to about 10 µm, about 1 µm to about 20 µm, about 1 µm to about 30 µm, about 1 µm to about 40 µm, about 1 µm to about 50 µm, about 2 µm to about 5 µm, about 2 µm to about 10 µm, about 2 µm to about 20 µm, about 2 µm to about 30 µm, about 2 µm to about 40 µm, about 2 µm to about 50 µm, about 5 µm to about 10 µm, about 5 µm to about 20 µm, about 5 µm to about 30 µm, about 5 µm to about 40 µm, about 5 µm to about 50 µm, about 10 µm to about 20 µm, about 10 µm to about 30 µm, about 10 µm to about 40 µm, about 10 µm to about 50 µm, about 20 µm to about 30 µm, about 20 µm to about 40 µm, about 20 µm to about 50 µm, about 30 µm to about 40 µm, about 30 µm to about 50 µm, or about 40 µm to about 50 µm. In some cases, the particles can have a mean particle size of about 0.1 µm, about 0.2 µm, about 0.5 µm, about 1 µm, about 2 µm, about 5 µm, about 10 µm, about 20

µm, about 30 µm, about 40 µm, or about 50 µm. The particles can have a mean particle size of about 1.5-15 µm in one example, about 3-5 µm in another example, about 0.2-1.5 µm in yet another example and about 0.5-0.9 µm in yet another example.

The pharmaceutical composition can comprise at least 50%, 60%, 70%, 80%, or 90% by weight of the particles having a particle size of about 0.2-15 µm. The pharmaceutical composition can comprise about 0.01%-50% by weight of the particles having an average particle size of about 1.5-15 µm and about 50% to 99.99% by weight of the particles having an average particle size of about 0.2-1.5 µm.

The neuroactive steroid of the pharmaceutical composition can comprise brexanolone, ganaxolone. zuranolone (SAGE-217) or a combination thereof.

In some cases, the neuroactive steroid can comprise brexanolone. The pharmaceutical composition can comprise in a range of from 5 mg/mL to 800 mg/mL brexanolone or any specific ranges of the neuroactive steroid disclosed hereabove or hereafter. The pharmaceutical composition can be a parenteral injection suspension comprising brexanolone. In some cases, the pharmaceutical composition can have large particles having a particle size in a range of from about 1.5 µm to about 15 µm and small particles having a particle size in a range of from about 0.2 µm to about 1.5 µm. A pharmaceutical composition comprising brexanolone can comprise particles having about 0.01% to about 50% of the small particles and about 50% to about 99.99% of the large particles, percentage based on the total weight of the particles. Such pharmaceutical composition comprising brexanolone can comprise in a range of from 0.01% to 50% in one example, 10% to 50% in another example, 15% to 50% in yet another example, 20% to 50% in yet another example, 25% to 50% in yet another example, 30% to 50% in yet another example, 40% to 50% in yet another example and 45% to 50% in yet another example of small particles; and in arrange of from 50% to 90% in one example, 55% to 90% in another example, 60% to 90% in yet another example, 65% to 90% in yet another example, 70% to 90% in yet another example, 75% to 90% in yet another example, 80% to 90% in yet another example and 85% to 90% in yet another example of large particles. In a particular example, the pharmaceutical composition can comprise about 10% to about 50% of the small particles and about 50% to about 90% of the large particles, percentage based on the total weight of the particles. In even further examples, the pharmaceutical composition can comprise about 0.1% to about 1% of the small particles and about 90% to about 99.9% of the large particles, percentage based on the total weight of the particles.

The neuroactive steroid can comprise ganaxolone and the pharmaceutical composition comprises in a range of from 100 mg/mL to 800 mg/mL ganaxolone or any specific ranges the neuroactive steroid disclosed herein. The pharmaceutical composition can be a parenteral injection suspension comprising ganaxolone. A pharmaceutical composition comprising ganaxolone can comprise about 0.01% to about 50% of small particles and about 50% to about 99.99% of large particles, percentage based on the total weight of the particles. Such pharmaceutical composition comprising ganaxolone can comprise particles in a range of from 0.01% to 50% in one example, 0.1% to 50% in another example, 1.0% to 50% in yet another example, 2.0% to 50% in yet another example, 4.0% to 50% in yet another example, 6.0% to 50% in yet another example, 8.0% to 50% in yet another example, 10% to 50% in one example, 15% to 50% in another example, 20% to 50% in yet another example, 25% to 50% in yet another example, 30% to 50% in yet another example, 40% to 50% in yet another example and 45% to 50% in yet another example of small particles; and in arrange of from 50% to 99.99% in one example, 55% to 99.99% in another example, 60% to 99.99% in yet another example, 65% to 99.99% in yet another example, 70% to 99.99% in yet another example, 75% to 99.99% in yet another example, 80% to 99.99% in yet another example and 85% to 99.99% in yet another example of large particles. In particular examples, the pharmaceutical composition can comprise about 0.01% to about 10% of the small particles and about 90% to about 99.99% of the large particles, percentage based on the total weight of the particles.

Figure 1B:
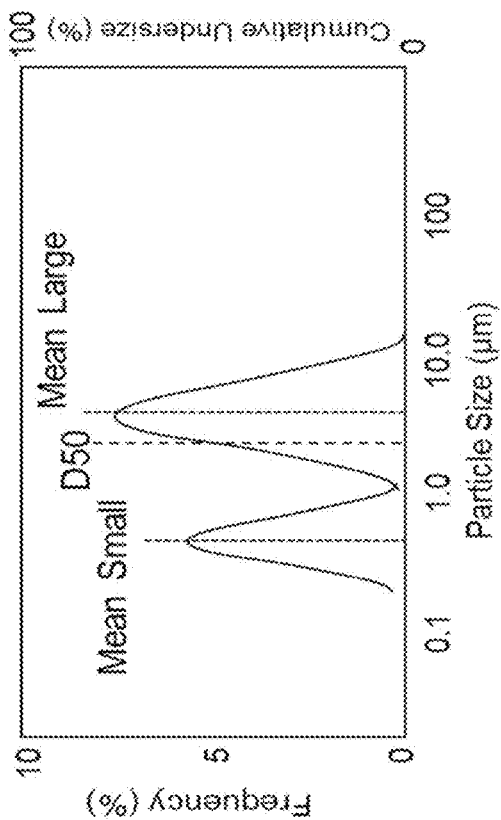
Figure 1C:
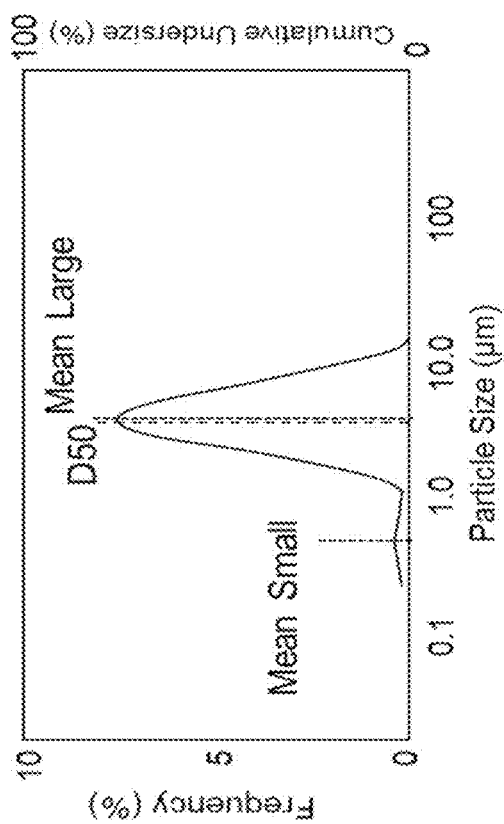
Figure 1D:
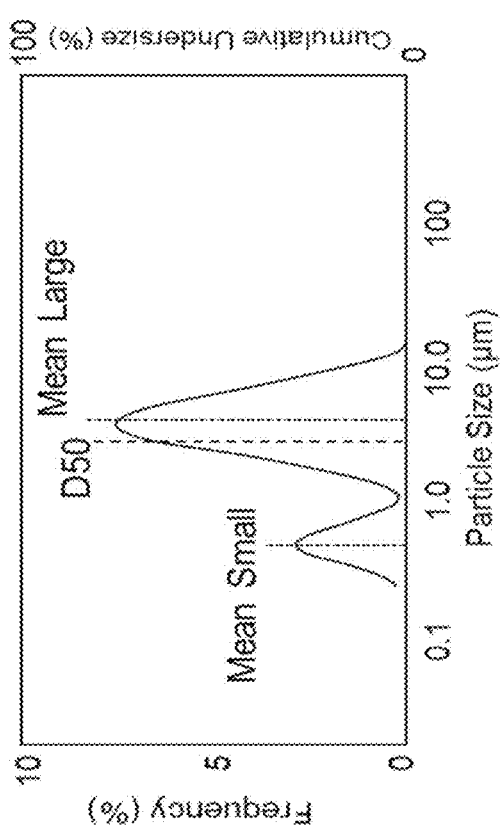

Schematic illustrations of particle size distributions are shown in FIG. 1A-FIG. 1D. In one example, a pharmaceutical composition can comprise minimum amounts, such as in a range of from 0.01% to 1% of small particles and mostly large particles (FIG. 1A). In this example, D50 can be very close to the mean particle size of the large particles. In another example, a pharmaceutical composition can comprise some amounts of small particles, such as in arrange of from 1% to 5% and 95% to 99% of large particles (FIG. 1B). In yet another example, a pharmaceutical composition comprises increasing amounts, such as 5% to 10% of small particles and 90% to 95% of large particles (FIG. 1C). In yet another example, a pharmaceutical composition comprises comparable amounts, such as 10% to 40% of small particles and 60% to 90% of large particles (FIG. 1D).

The pharmaceutical composition can be substantially free of cyclodextrins. In examples, the pharmaceutical composition is substantially free of cyclodextrins meaning that the pharmaceutical composition comprises 0 to 0.1%, 0 to 0.01%, 0 to 0.001%, 0 to 0.0001% or less cyclodextrins, all percentages based on the total weight of the pharmaceutical composition.

The pharmaceutical composition can be substantially free of sulfobutyl ether β-cyclodextrin. In examples, the pharmaceutical composition is substantially free of sulfobutyl ether β-cyclodextrin meaning that the pharmaceutical composition comprises 0 to 0.1%, 0 to 0.01%, 0 to 0.001%, 0 to 0.0001% or less sulfobutyl ether β-cyclodextrin, all percentages based on the total weight of the pharmaceutical composition.

In further examples, the pharmaceutical composition can be a liquid suspension for intramuscular (IM) or subcutaneous (SC) injection.

Also disclosed is a process for producing the pharmaceutical composition disclosed herein. In some cases, the process can comprise: a) mixing a composition comprising the neuroactive steroid with one or more pharmaceutically acceptable excipients; and b) milling the composition to produce a population of particles to produce the pharmaceutical composition. In some cases, the process can comprise: a) milling a composition comprising the neuroactive steroid to produce a population of particles; and b) mixing the composition with one or more pharmaceutically acceptable excipients to produce the pharmaceutical composition. In some cases, the process comprises crystalizing the brexanolone polymorph Form A from one or more solvents selected from the group consisting of dichloromethane (DCM), tetrahydrofuran (THF), ethyl acetate (EtOAc), dimethyl sulfoxide (DMSO), toluene, 2-propanol:water (9:1), methanol (MeOH), 2-propanol (IPA), methyl t-butyl ether (MTBE), isopropyl ether (IPE), acetonitrile (MeCN), and water. In some cases, the one or more solvents do not comprise acetonitrile. In some cases, the process further comprises: a) mixing the brexanolone polymorph Form A with one or more pharmaceutically acceptable excipients to form a composition; and b) milling said composition to produce a population of particles of said pharmaceutical composition. In some cases, the process further comprises: a) milling a composition comprising the brexanolone polymorph Form A to produce a population of particles; and b) mixing said composition with one or more pharmaceutically acceptable excipients to produce said pharmaceutical composition. In some cases, the pharmaceutical composition is a liquid suspension for intramuscular or subcutaneous injection.

In some cases, disclosed herein is a method for producing a pharmaceutical composition comprising particles, comprising: producing a particle mixture comprising at least one neuroactive steroid and one or more pharmaceutical acceptable excipients; milling a first portion of the particle mixture to produce a large particle mixture, wherein at least 50% of the large particle mixture are large particles having a particle size in a range of from about 1.5 µm to about 15 µm, percentage based on the total weight of the particle mixture; and producing the pharmaceutical composition comprising the particles comprising about 50% to 99.99% of the large particles, percentage based on the total weight of the particles.

The neuroactive steroid can be selected from tetrahydrodeoxycorticosterone (THDOC), androstane, androstane 3α-androstanediol, cholestane cholesterol, pregnane, pregnane pregnanolone (eltanolone), allopregnanolone, brexanolone, ganaxolone, zuranolone (SAGE-217) or a combination thereof. In one example, the neuroactive steroid is brexanolone. In another example, the neuroactive steroid is ganaxolone. In another example, the neuroactive steroid is zuranolone.

Commercially available or proprietary neuroactive steroids API can be suitable as a starting material for producing the particle mixture. Typically, the commercially available neuroactive steroids API can have a large particle size. For example, a commercial brexanolone can have a particle size of about 7 to 10 µm in diameter. In another example, a commercial ganaxolone can have a particle size of about 40 to 50 µm. The milling process can reduce particles to a range of suitable sizes.

Typical milling media, such milling beads can be used for milling the particles. The milling bead can have a diameter of 0.1 mm to about 1 mm. In examples, a rotary milling process with a rotation speed of 300 to 600 rpm can be suitable. The particles can be milled for 10 to 40 minutes, 10 to 40 cycles or a time and cycles sufficient to produce particles of desired size range. The milling can be conducted in the presence of one or more excipients disclosed herein.

The large particles can have a mean particle size in a range of from 1.5 µm to about 15 µm in one example, 1.5 µm to 10 µm in another example, 1.5 µm to 8,000 µm in yet another example, 1.5 µm to 6.0 µm in yet another example and 1.5 µm to 4.5 µm in yet another example. In additional examples, the large particles can have a mean particle size in a range of from 2.0 to 6.0 µm. In further embodiments, the large particles can have a mean particle size in a range of from 2.0 to 5.0 µm. In one further example, the large particles can have a particle size of about 2.0 µm to about 4.5 µm.

The process or method can further comprise: milling a second portion of the particle mixture to produce a small particle mixture, wherein the small particle mixture comprises small particles having a particle size in a range of from about 0.2 µm to about 1.5 µm. In some cases, the pharmaceutical composition is produced by mixing the large particle mixture and the small particle mixture to form the particles comprising about 50% to 99.99% of the large particles and 0.01% to 50% of the small particles, percentage based on the total weight of the particles.

The first portion and the second portion can be the same or different. In some examples, the first portion and the second portion are the same and the particle mixture is configured to be milled to comprise the large particles and the small particles. In some further examples, the second portion can a part of the first portion and further milled to produce the small particles. In yet some examples, the first portion and the second portion are divided from the original particle mixture and milled separately to produce the large particle and the small particles, respectively.

The small particles can have a mean particle size in a range of from 0.2 µm to about 1.5 µm in one example, 0.2 µm to 1.2 µm in another example, 0.2 µm to 1.0 µm in yet another example, 0.2 µm to 0.8 µm in yet another example and 0.2 µm to 0.7 µm in yet another example. In further examples, the small particles can have a mean particle size in a range of from 0.4 to 1.3 µm. In additional examples, the small particles can have a mean particle size in a range of from 0.5 to 0.9 µm. In an even further example, the small particles can have a mean particle size of about 0.7 µm.

The suitable pharmaceutical acceptable excipients can be selected from acacia, animal oils, benzyl alcohol, benzyl benzoate, calcium stearate, carbomers, cetostearyl alcohol, cetyl alcohol, cholesterol, cyclodextrins, dextrose, diethanolamine, emulsifying wax, ethylene glycol palmitostearate, glycerin, glycerin monostearate, glycerol stearate, glyceryl monooleate, glyceryl monostearate, histidine, hydrochloric acid, hydrous, histidine, hydrochloric acid, hydroxypropyl cellulose, hydroxypropyl-β-cyclodextrin (HPBCD), hypromellose (hydroxypropyl methylcellulose (HPMC)), lanolin, lanolin alcohols, lecithin, medium-chain triglycerides, metallic soaps, methylcellulose, mineral oil, monobasic sodium phosphate, monoethanolamine, oleic acid, polyyethylene glycols (PEG 3350, PEG 4000, PEG 6000), polyoxyethylene-polyoxypropylene copolymer (poloxamer), polyoxyethylene alkyl ethers, polyoxyethylene castor oil, polyoxyethylene castor oil derivatives, polyoxyethylene sorbitan fatty acid esters, polyoxyethylene stearates, polysorbate, polyoxyethylene (20) sorbitan monolaurate (Tween 20, Polysorbate 20), polyoxyethylene (20) sorbitan monooleate (Tween 80, Polysorbate 80), povidone, propylene glycol alginate, saline, sodium chloride, sodium citrate, sodium citrate dihydrate, sodium hydroxide, sodium lauryl sulfate, sodium phosphate monobasic, sodium phosphate dibasic, sorbitan esters, stearic acid, stearyl alcohol, sunflower oil, tragacanth, triethanolamine, vegetable oils, water, xanthan gum, and a combinations thereof.

In some cases, the pharmaceutical acceptable excipients can comprise dextrose, glycerin, histidine, hydrochloric acid, hydroxypropyl cellulose, hydroxypropyl-β-cyclodextrin (HPBCD), hypromellose (hydroxypropyl methylcellulose (HPMC)), polyoxyethylene (20) sorbitan monolaurate (Tween 20, Polysorbate 20), polyyethylene glycols (PEG 3350, PEG 4000, PEG 6000), polyoxyethylene-polyoxypropylene copolymer (Poloxamer 188, Poloxamer 407), polyoxyethylene (20) sorbitan monooleate (Tween 80, Polysorbate 80), saline, sodium chloride, sodium citrate, sodium citrate dihydrate, sodium lauryl sulfate, sodium phosphate monobasic, sodium phosphate dibasic, or a combinations thereof.

In some cases, the pharmaceutical composition can be formulated as a parenteral injection suspension and/or suitable for oral administration, intramuscular (IM) injection, subcutaneous (SC) injection, intravenous (IV) injection or a combination thereof.

In some cases, the neuroactive steroid can comprise brexanolone and the pharmaceutical composition can comprise in a range of from 5 mg/mL to 800 mg/mL brexanolone or any specific ranges the neuroactive steroid disclosed herein, for example from 100 mg/mL to 800 mg/mL. The pharmaceutical composition can be formulated as a parenteral injection suspension comprising brexanolone. A pharmaceutical composition comprising brexanolone can comprise particles having about 0.01% to about 50% of the small particles and about 50% to about 99.99% of the large particles, percentage based on the total weight of the particles. Such pharmaceutical composition comprising brexanolone can be configured to comprise particles in a range of from 0.01% to 50% in one example, 10% to 50% in another example, 15% to 50% in yet another example, 20% to 50% in yet another example, 25% to 50% in yet another example, 30% to 50% in yet another example, 40% to 50% in yet another example and 45% to 50% in yet another example of small particles; and in arrange of from 50% to 90% in one example, 55% to 90% in another example, 60% to 90% in yet another example, 65% to 90% in yet another example, 70% to 90% in yet another example, 75% to 90% in yet another example, 80% to 90% in yet another example and 85% to 90% in yet another example of large particles. In a particular example, the pharmaceutical composition can comprise about 10% to about 50% of the small particles and about 50% to about 90% of the large particles, percentage based on the total weight of the particles. In even further examples, the pharmaceutical composition can be configured to comprise about 0.1% to about 1% of the small particles and about 90% to about 99.9% of the large particles, percentage based on the total weight of the particles.

The neuroactive steroid can comprise ganaxolone and the pharmaceutical composition can comprise in a range of from 100 mg/mL to 800 mg/mL ganaxolone or any specific ranges the neuroactive steroid disclosed herein. The pharmaceutical composition can be formulated as a parental injection suspension comprising ganaxolone. A pharmaceutical composition comprising ganaxolone can be configured to comprise about 0.01% to about 50% of small particles and about 50% to about 99.99% of large particles, percentage based on the total weight of the particles. Such pharmaceutical composition comprising ganaxolone can be configured to comprise in a range of from 0.01% to 50% in one example, 0.1% to 50% in another example, 1.0% to 50% in yet another example, 2.0% to 50% in yet another example, 4.0% to 50% in yet another example, 6.0% to 50% in yet another example, 8.0% to 50% in yet another example, 10% to 50% in one example, 15% to 50% in another example, 20% to 50% in yet another example, 25% to 50% in yet another example, 30% to 50% in yet another example, 40% to 50% in yet another example and 45% to 50% in yet another example of small particles; and in arrange of from 50% to 99.99% in one example, 55% to 99.99% in another example, 60% to 99.99% in yet another example, 65% to 99.99% in yet another example, 70% to 99.99% in yet another example, 75% to 99.99% in yet another example, 80% to 99.99% in yet another example and 85% to 99.99% in yet another example of large particles. In particular examples, the pharmaceutical composition can comprise about 0.01% to about 10% of the small particles and about 90% to about 99.99% of the large particles, percentage based on the total weight of the particles. In any of embodiments or examples of the process or method, the particles can be stabilized particles disclosed herein.

In some cases, one advantage of the pharmaceutical composition is that it can comprise small particles and large particles and can provide controlled releases of brexanolone, ganaxolone, zuranolone (SAGE-217), or combination thereof. Not wishing to be bound by a particular theory or a mechanism, applicants believe that the smaller particles can provide early or fast release, while larger particles provide extended or sustained release. By optimizing the ratio of small particles and large particles, an optimized release profile can be achieved for best treatment of the disease.

In some cases, another advantage of the disclosed pharmaceutical composition is that, due to the optimized release profile, it can be administered to a subject in a short administration time period avoiding long injection time that are associated with the drugs currently available, such as ZULRESSO™.

Also disclosed herein is a method for treating a disease in a subject in need thereof, the method comprising administering the subject a pharmaceutical composition disclosed herein or a pharmaceutical composition produced by a process disclosed herein, via intramuscular (IM) injection, subcutaneous (SC) injection, intravenous (IV) injection or a combination thereof. In some examples, intramuscular (IM) injection or subcutaneous (SC) injection is preferred. In some cases, the method can comprise: administering the pharmaceutical composition disclosed herein to a subject by intramuscular or subcutaneous injection.

In some cases, disclosed is a method of treating a disease in a subject in need thereof, comprising: administering a pharmaceutical composition comprising a pharmaceutically effective amount of a neuroactive steroid to the subject by intramuscular or subcutaneous injection with a single dose in a range of from 0.5 to 10 mg per kilogram of body weight, wherein the neuroactive steroid is a positive modulator of gamma-aminobutyric acid type A (GABA$_A$) receptor; and wherein plasma concentration of the neuroactive steroid reaches a maximum plasma concentration ($C_{max}$) in the subject in about 30 minutes to 6 hours and maintains the plasma concentration in the subject of more than about 5% of the $C_{max}$ for at least about 5 days, after intramuscular or subcutaneous injection to the subject.

As mentioned above, the body weight can refer to the body weight of a subject, such as a human patient. The range include single doses of 0.5, 10 mg per kg of body weight and a continuous range including every value between the 0.5 and 10 mg per kg of body weight. For an animal subject, the single dose can be different as mentioned above.

In some cases, the pharmaceutical composition can be administered to the subject via intramuscular (IM) injection, subcutaneous (SC) injection, intravenous (IV) injection or a combination thereof. The pharmaceutical composition can be administered to a subject in a bolus injection, in a continuous injection, or a combination thereof. The pharmaceutical composition can be administered to a subject within a time period in a range of from 1 second to about 180 minutes. The pharmaceutical composition can be administered to a subject within a time period in a range of from about 1 second to about 180 minutes in one example, 1 minute to about 180 minutes in another example, 5 minutes to about 180 minutes in yet another example, 10 minutes to about 180 minutes in yet another example, 20 minutes to about 180 minutes in yet another example, 40 minutes to about 180 minutes in yet another example, 50 minutes to about 180 minutes in yet another example, 60 minutes to about 180 minutes in yet another example, or any time one value within the range. In further examples, the pharmaceutical composition can be administered to a subject within a time period in a range of from 1 second to about 150 minutes, 1 second to about 100 minutes, 1 second to about 80 minutes, 1 second to about 60 minutes, 1 second to about 30 minutes, 1 second to about 10 minutes, 1 second to about 5 minutes and 1 seconds to about 1 minute in yet another example. In a particular example, the pharmaceutical composition can be administered to a subject with one shot single injection. In additional examples, the pharmaceutical composition can be administered to a subject with two or more injections.

In some cases, the disease can be selected from anxiety, mood disorder, massive depression disorder, postpartum disorder, Alzheimer disease, Parkinson disease, epilepsy, focal onset seizures, PCDH19 pediatric epilepsy, pediatric genetic epilepsies, CDKL5 Deficiency Disorder (CDD), catamenial epilepsy, infantile spasms, Fragile X syndrome, depression, postpartum depression, and premenstrual syndrome. In some cases, the disease can be postpartum depression. The subject can have prior history of depression. In some cases, the subject can have prior history of postpartum depression.

Also disclosed herein is a use of a composition comprising a neuroactive steroid for manufacturing a medicament for treating a disease, wherein the composition is a pharmaceutical composition disclosed herein. The disease can be selected from anxiety, mood disorder, massive depression disorder, postpartum disorder, Alzheimer disease, Parkinson disease, epilepsy, focal onset seizures, PCDH19 pediatric epilepsy, pediatric genetic epilepsies, CDKL5 Deficiency Disorder (CDD), catamenial epilepsy, infantile spasms, Fragile X syndrome, depression, postpartum depression, and premenstrual syndrome. The neuroactive steroid can be selected from tetrahydrodeoxycorticosterone (THDOC), androstane, androstane 3α-androstanediol, cholestane cholesterol, pregnane, pregnane pregnanolone (eltanolone), allopregnanolone, brexanolone, ganaxolone, zuranolone (SAGE-217), and a combination thereof.

In some cases, the composition comprises a neuroactive steroid for use in a method for the treatment of a disease, wherein the neuroactive steroid is a positive modulator of gamma-aminobutyric acid type A (GABA$_A$) receptor; and wherein plasma concentration of the neuroactive steroid reaches a maximum plasma concentration ($C_{max}$) in about 30 minutes to 6 hours and maintains the plasma concentration of more than about 5% of the $C_{max}$ for at least about 5 days, after a single dose of the neuroactive steroid by intramuscular or subcutaneous injection. The disease can be selected from anxiety, mood disorder, massive depression disorder, postpartum disorder, Alzheimer disease, Parkinson disease, epilepsy, focal onset seizures, PCDH19 pediatric epilepsy, pediatric genetic epilepsies, CDKL5 Deficiency Disorder (CDD), catamenial epilepsy, infantile spasms, Fragile X syndrome, depression, postpartum depression, and premenstrual syndrome. The neuroactive steroid can be selected from tetrahydrodeoxycorticosterone (THDOC), androstane, androstane 3α-androstanediol, cholestane cholesterol, pregnane, pregnane pregnanolone (eltanolone), allopregnanolone, brexanolone, ganaxolone, zuranolone (SAGE-217), and a combination thereof. In some cases, the composition is a pharmaceutical composition disclosed herein. In some cases, the method is a method disclosed above.

In some cases, disclosed herein is a use of particles comprising at least one neuroactive steroid and one or more pharmaceutical acceptable excipients for manufacturing a medicament for treating a disease, wherein, the particles comprise large particles having a particle size in a range of from about 1.5 μm to about 15 μm and small particles having a particle size in a range of from about 0.2 μm to about 1.5 μm; and wherein, about 0.01% to about 50% of the particles are small particles and about 50% to 99.99% of the particles are large particles, percentage based on the total weight of the particles. The neuroactive steroid can be selected from tetrahydrodeoxycorticosterone (THDOC), androstane, androstane 3α-androstanediol, cholestane cholesterol, pregnane, pregnane pregnanolone (eltanolone), allopregnanolone, brexanolone, ganaxolone, zuranolone (SAGE-217), and a combination thereof. In some cases, the large particles can have a mean particle size in a range of from 2.0 to 6.0 μm in one example, 3.0 to 5.0 μm in another example, 0.4 to 1.3 μm in yet another example, and 0.5 to 0.9 μm in yet another example. The particles can be stabilized particles disclosed herein.

In some cases, the pharmaceutical acceptable excipients can comprise surfactant, emulsifier, filler, carrier, isotonicfier, dispersing agent, viscosity modifier, resuspending agent, buffer, and a combination thereof. In some cases, the pharmaceutical acceptable excipients comprise acacia, animal oils, benzyl alcohol, benzyl benzoate, calcium stearate, carbomers, cetostearyl alcohol, cetyl alcohol, cholesterol, cyclodextrins, dextrose, diethanolamine, emulsifying wax, ethylene glycol palmitostearate, glycerin, glycerin monostearate, glycerol stearate, glyceryl monooleate, glyceryl monostearate, hydrous, histidine, hydrochloric acid, hydroxypropyl cellulose, hydroxypropyl-β-cyclodextrin (HPBCD), hypromellose (hydroxypropyl methylcellulose (HPMC)), lanolin, lanolin alcohols, lecithin, medium-chain triglycerides, metallic soaps, methylcellulose, mineral oil, monobasic sodium phosphate, monoethanolamine, oleic acid, polyyethylene glycols (PEG 3350, PEG 4000, PEG 6000), polyoxyethylene-polyoxypropylene copolymer (poloxamer), polyoxyethylene alkyl ethers, polyoxyethylene castor oil, polyoxyethylene castor oil derivatives, polyoxyethylene sorbitan fatty acid esters, polyoxyethylene stearates, polysorbate, polyoxyethylene (20) sorbitan monolaurate (Tween 20, Polysorbate 20), polyoxyethylene (20) sorbitan monooleate (Tween 80, Polysorbate 80), povidone, propylene glycol alginate, saline, sodium chloride, sodium citrate, sodium citrate dihydrate, sodium hydroxide, sodium lauryl sulfate, sodium phosphate monobasic, sodium phosphate dibasic, sorbitan esters, stearic acid, stearyl alcohol, sunflower oil, tragacanth, triethanolamine, vegetable oils, water, xanthan gum, or a combinations thereof.

In some cases, the pharmaceutical acceptable excipients can comprise dextrose, glycerin, histidine, hydrochloric acid, hydroxypropyl cellulose, hydroxypropyl-β-cyclodextrin (HPBCD), hypromellose (hydroxypropyl methylcellulose (HPMC)), polyoxyethylene (20) sorbitan monolaurate (Tween 20, Polysorbate 20), polyyethylene glycols (PEG 3350, PEG 4000, PEG 6000), polyoxyethylene-polyoxypropylene copolymer (Poloxamer 188, Poloxamer 407), polyoxyethylene (20) sorbitan monooleate (Tween 80, Polysorbate 80), saline, sodium chloride, sodium citrate, sodium citrate dihydrate, sodium lauryl sulfate, sodium phosphate monobasic, sodium phosphate dibasic, or a combinations thereof. In some cases, the pharmaceutical composition is a parenteral injection suspension.

In some cases, the neuroactive steroid can comprise brexanolone and the pharmaceutical composition comprises in a range of from 80 mg/mL to 400 mg/mL brexanolone. In some cases, the neuroactive steroid can comprise ganaxolone and the pharmaceutical composition comprises in a range of from 80 mg/mL to 400 mg/mL ganaxolone.

In some cases, the pharmaceutical composition can comprise about 10% to about 50% of the small particles and about 50% to about 90% of the large particles, percentage based on the total weight of the particles. In some cases, the pharmaceutical composition can comprise about 0.01% to about 50% of the small particles and about 50% to about 99.99% of the large particles, percentage based on the total weight of the particles.

In some cases, the disease can be selected from anxiety, mood disorder, massive depression disorder, postpartum disorder, Alzheimer disease, Parkinson disease, epilepsy, focal onset seizures, PCDH19 pediatric epilepsy, pediatric genetic epilepsies, CDKL5 Deficiency Disorder (CDD), catamenial epilepsy, infantile spasms, Fragile X syndrome, depression, postpartum depression, and premenstrual syndrome.

Also disclosed is a method for producing a pharmaceutical composition for controlled release of at least one neuroactive steroid comprising brexanolone, ganaxolone, zuranolone (SAGE-217) or a combination thereof. The method comprises: producing large particles having a particle size in a range of from about 1.5 µm to about 15 µm and small particles having a particle size in a range of from about 0.2 µm to about 1.5 µm; mixing the small particles and the large particles to produce particles, wherein, about 0.01% to about 50% of the particles are the small particles and about 50% to 99.99% of the particles are the large particles, percentage based on the total weight of the particles; and producing the pharmaceutical composition comprising the particles by adjusting a ratio of the small particles and the large particles so that the pharmaceutical composition is configured to release the neuroactive steroid within 0.1 to 1 hour in a subject after administered to the subject in need thereof and continue to release the neuroactive steroid in the subject for a time period in a range of from 10 hours to about 200 hours after administered to the subject.

Crystal Form of Brexanolone

Also disclosed is a pharmaceutical composition, comprising a brexanolone polymorph Form A, characterized by having at least 2, 3, 4, 5, 6, 7, 8, 9, or 10 of the following peaks in an X-ray Powder Diffraction (XRPD) diffractogram, at 7.25, 8.88, 11.46, 14.50, 14.78, 17.77, 18.15, 18.32, 18.61, and 19.99±0.1° 2θ.

In some cases, the pharmaceutical composition is a liquid suspension. In some cases, the pharmaceutical composition is for intramuscular or subcutaneous injection. In some cases, the liquid suspension comprises the brexanolone polymorph Form A. In some cases, the brexanolone polymorph Form A has a chemical purity of greater than 80%, 85%, 90%, 95%, 96%, 97%, 98%, or 99% (w/w). In some cases, the chemical purity is quantified by HPLC. In some cases, the brexanolone polymorph Form A has a melting point of about 170-180° C. In some cases, the brexanolone polymorph Form A has a melting point of about 174° C.

In some cases, the brexanolone polymorph Form A is crystalized from one or more solvents selected from the group consisting of dichloromethane (DCM), tetrahydrofuran (THF), ethyl acetate (EtOAc), dimethyl sulfoxide (DMSO), toluene, 2-propanol:water (9:1), methanol (MeOH), 2-propanol (IPA), methyl t-butyl ether (MTBE), isopropyl ether (IPE), acetonitrile (MeCN), and water. In some cases, the one or more solvents do not comprise acetonitrile.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Example 1: Brexanolone Suspensions

Figure 2A:
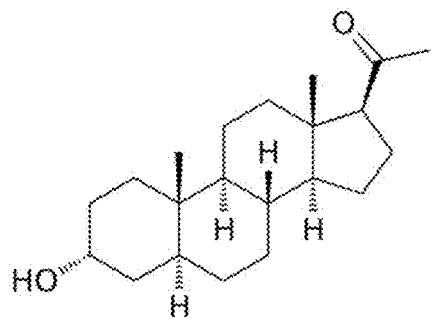
FIG. 2A-FIG. 2E. Examples of pharmaceutical compositions comprising brexanolone.

Brexanolone was purchased from commercial vender as an active pharmaceutical ingredient (API) (FIG. 2A). The article size of the commercial brexanolone is about 7 to 8 µm.

The commercial brexanolone was milled in the presence of water, saline, dextrose, HPMC, TWEEN 80, poloxamer 407 and glycerin with a rotation speed of about 300 to 500 rpm for about 20 to 30 minutes. The milling was performed for 1-5 cycles depending on the desired particle size. The milling media used was beads having a diameter of 0.1 to 1.0 mm.

Figure 2B:
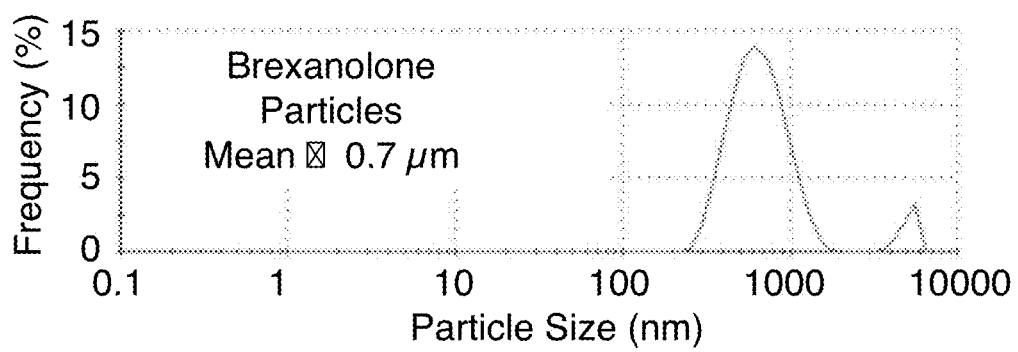
Figure 2C:
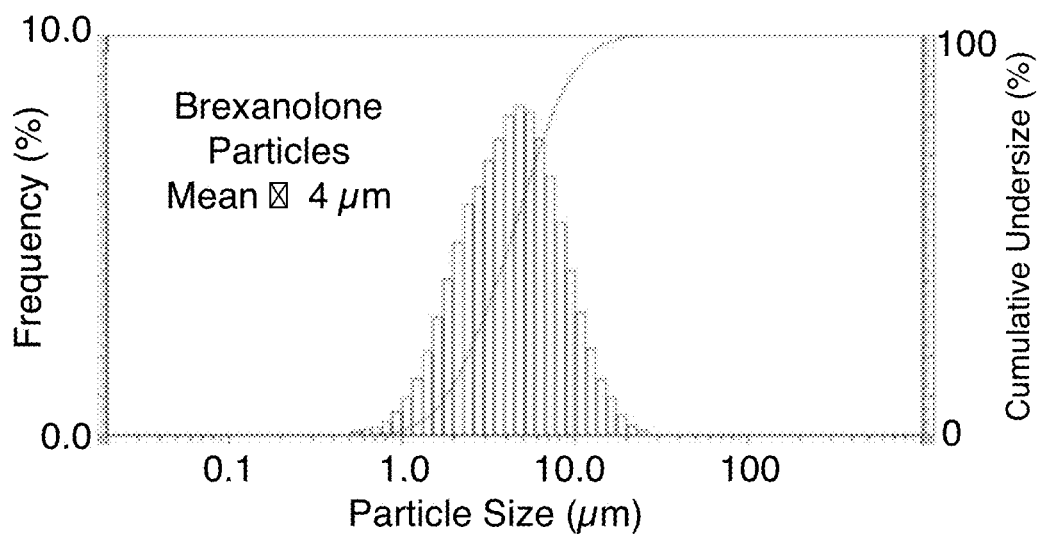

By controlling the milling parameters, two sets of particles sizes were selected. One was small particle having a mean particle size of about 0.7 µm (FIG. 2B) and the other was large particle having a mean particle size of about 4.0 µm (FIG. 2C).

Example 2: Pharmacokinetics (PKs) of Brexanolone Compositions in Rats

Figure 2D:
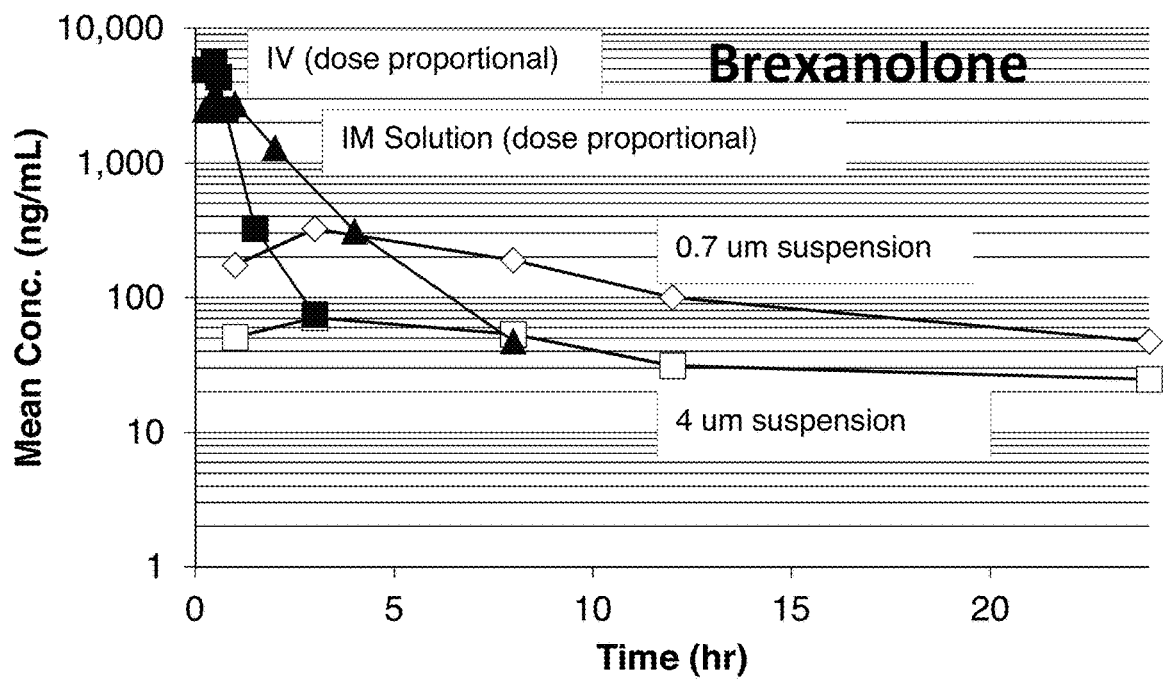
Figure 2E:
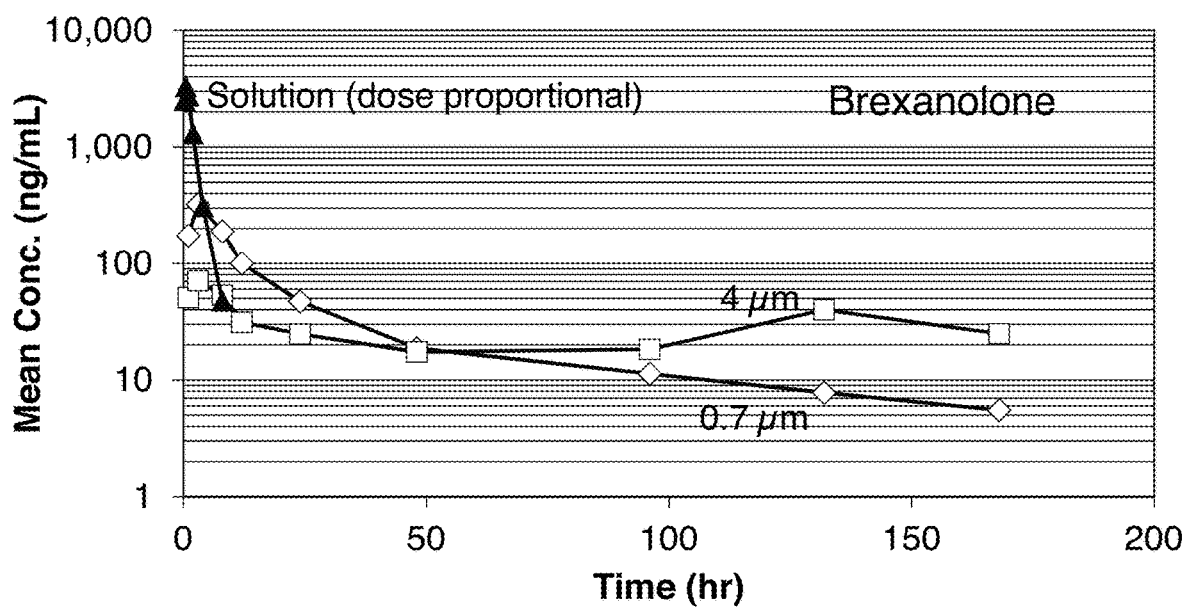

Suspensions of the 0.7 µm particles and the 4.0 µm particles were separately injected into rats via intramuscular (IM) injection at a dosage of 25 mg/kg of brexanolone. For comparison, comparative brexanolone solutions were injected via intramuscular (IM) injection at a dosage of 12.5 mg/kg, or intravenous (IV) injection at 1 mg/kg. Plasma brexanolone concentration were measured at indicated time points. Data are shown in FIG. 2D-FIG. 2E. PKs for the solutions were adjusted to have proportional doses.

Example 3: Injectable Brexanolone Pharmaceutical Compositions

A first brexanolone composition is produced using the suspension of the 0.7 µm particles prepared above to have a desired pharmacokinetics profile.

A second brexanolone composition is produced by mixing the suspensions of the 0.7 µm particles and 4.0 µm particles prepared above. The composition is adjusted to have about 10% of the 0.7 µm particles and about 90% of the 4.0 µm particles to have a desired pharmacokinetics profile.

A third brexanolone composition is produced by mixing the suspensions of the 0.7 µm particles and 4.0 µm particles prepared above. The composition is adjusted to have about 30% of the 0.7 µm particles and about 70% of the 4.0 µm particles to have a desired pharmacokinetics profile.

A fourth brexanolone composition is produced by mixing the suspensions of the 0.7 µm particles and 4.0 µm particles prepared above. The composition is adjusted to have about 40% of the 0.7 µm particles and about 60% of the 4.0 µm particles to have a desired pharmacokinetics profile.

A fifth brexanolone composition is produced by mixing the suspensions of the 0.7 µm particles and 4.0 µm particles prepared above. The composition is adjusted to have about 50% of the 0.7 µm particles and about 50% of the 4.0 µm particles to have a desired pharmacokinetics profile.

A sixth brexanolone composition is produced using the suspension of the 4 µm particles prepared above to have a desired pharmacokinetics profile.

Example 4: Ganaxolone Suspensions

Figure 3A:
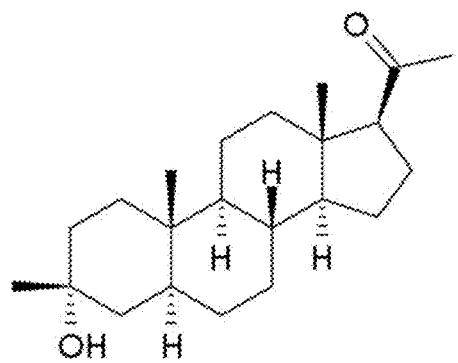
FIG. 3A-FIG. 3E. Examples of pharmaceutical compositions comprising ganaxolone.

Ganaxolone was purchased from commercial vender as an active pharmaceutical ingredient (API) (FIG. 3A). The article size of the commercial brexanolone is about 47 µm.

The commercial ganaxolone was milled in the presence of water, saline, 1 mg/mL TWEEN 80 and 5 mg/mL HPMC with a rotation speed of about 200 rpm for about 20 minutes. The milling was performed for 3 cycles. The milling media used was beads having a diameter of 1.0 mm.

Figure 3B:
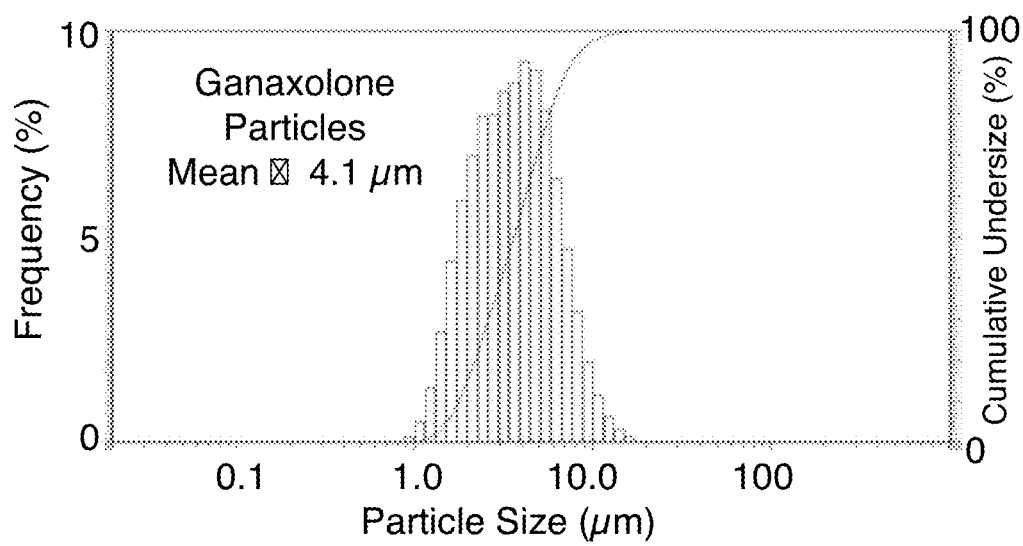
Figure 3C:
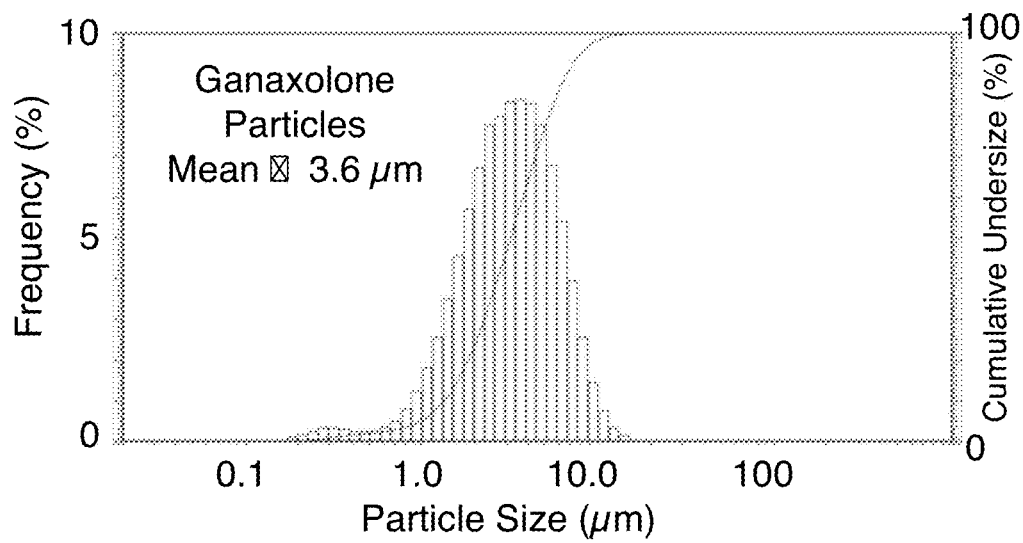

The milled particles had less than 1% of particles having sizes less than 1.5 µm with mean sizes of about 4.1 µm (FIG. 3B) about 3.6 µm (FIG. 3C) in two batches. Particles of having a mean particle size of about 1.0 µm were also produced.

Example 5: Pharmacokinetics (PKs) of Ganaxolone Compositions in Rats

Figure 3D:
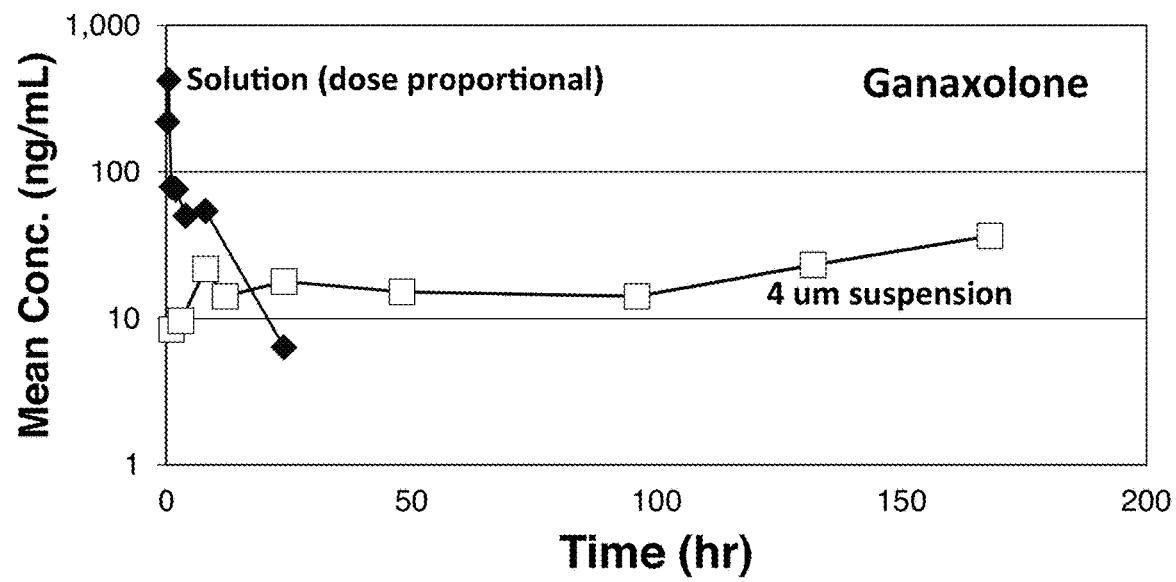
Figure 3E:
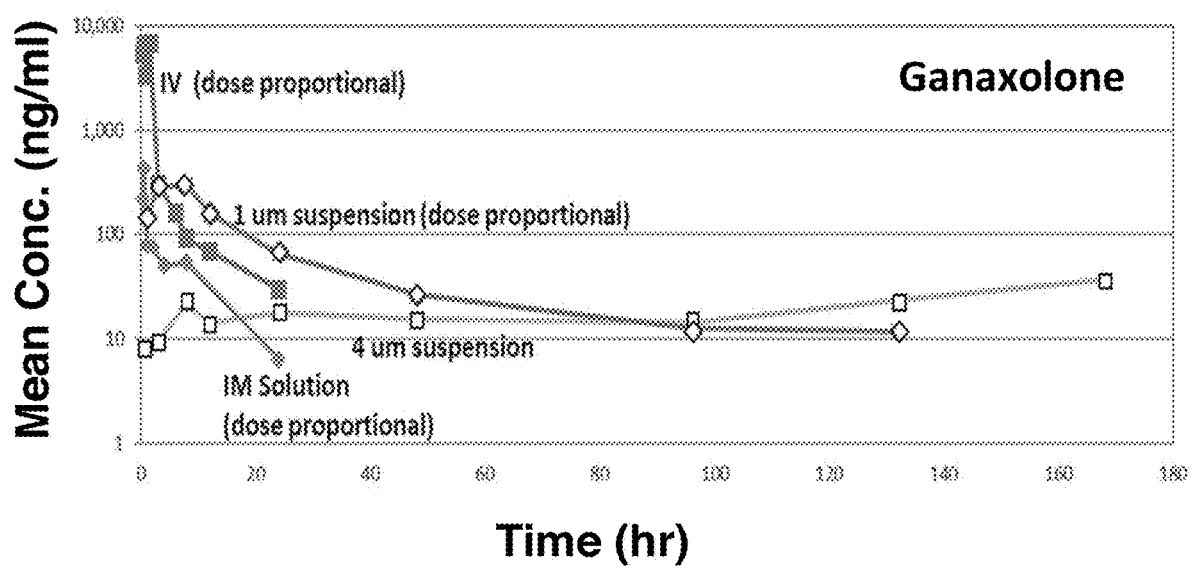

Suspensions of the particles having 1 µm and 4.1 µm were separately injected into rats via intramuscular (IM) injection at a dosage of 25 mg/kg of ganaxolone. For comparison, comparative ganaxolone solutions were injected via intramuscular (IM) injection at a dosage of 12.5 mg/kg, or intravenous (IV) injection at 1 mg/kg. Plasma brexanolone concentration were measured at indicated time points. Data are shown in FIG. 3D and FIG. 3E. PKs for the solutions were adjusted to have proportional doses.

Example 6: Injectable Ganaxolone Pharmaceutical Compositions

A first ganaxolone composition is produced using the suspension of the 1 µm particles prepared above to have a desired pharmacokinetics profile.

A second ganaxolone composition is produced by mixing the suspensions of the 1 µm particles and 4.1 µm particles prepared above. The composition is adjusted to have about 10% of the 1 µm particles and about 90% of the 4.1 µm particles to have a desired pharmacokinetics profile.

A third ganaxolone composition is produced by mixing the suspensions of the 1 µm particles and 4.1 µm particles prepared above. The composition is adjusted to have about 30% of the 1 µm particles and about 70% of the 4.1 µm particles to have a desired pharmacokinetics profile.

A fourth ganaxolone composition is produced by mixing the suspensions of the 1 µm particles and 4.1 µm particles prepared above. The composition is adjusted to have about 40% of the 1 µm particles and about 60% of the 4.1 µm particles to have a desired pharmacokinetics profile.

A fifth ganaxolone composition is produced by mixing the suspensions of the 1 µm particles and 4.1 µm particles prepared above. The composition is adjusted to have about 50% of the 1 µm particles and about 50% of the 4.1 µm particles to have a desired pharmacokinetics profile.

A sixth ganaxolone composition is produced using the suspension of the 4.1 µm particles prepared above to have a desired pharmacokinetics profile.

Example 7: Brexanolone Crystal Form Screening

Brexanolone was purchased from commercial vender and gently grounded prior to dispensing. The brexanolone sample was analyzed by the following analytical techniques: FT-Raman spectroscopy, FT-IR spectroscopy, Differential calorimeter (DSC), Thermogravimetric analysis (TGA-IR), Polarized light microscopy (PLM), and Powder X-ray diffraction (PXRD). The sample was determined to be a white crystalline powder consisting of irregular particles with a wide range of size, including large brittle chunks. The DSC analysis showed a melting endotherm at 174° C. ($\Delta H=101$ J/g). TGA analysis showed negligible (<0.1%) weight loss between 25-175° C., indicating that the material is non-solvated.

Solubility of the supplied brexanolone was determined by visual assessment of dissolution in various solvents at RT (~22° C.) and 40° C. Aliquots of solvent were added to a fixed amount of brexanolone (~10 mg) at room temperature until the dissolution point or a maximum volume of 1.8 mL was reached. All samples were then heated to 40° C. for 1 h and dissolution was observed. As shown in Error! Reference source not found, at RT brexanolone exhibited low solubility (<6 mg/mL) in water, moderate solubility (6-52 mg/mL) in MeCN, IPE, MTBE, IPA, MeOH, a mixture of IPA:water (9:1, v:v), toluene, DMSO, EtOAc and high solubility (>96 mg/mL) in THF, and DCM.

TABLE 1

Solubility of brexanolone at RT and 40° C.

| # | Solvent (v:v) | Solubility at RT [mg/mL] | Solubility at 40° C. [mg/mL] |
|---|---|---|---|
| 1 | Dichloromethane (DCM) | 108-432 | >108 |
| 2 | Tetrahydrofuran (THF) | 96-384 | >96 |
| 3 | Ethyl Acetate (EtOAc) | 21-52 | >21 |
| 4 | Dimethyl sulfoxide (DMSO) | 20-49 | >20 |
| 5 | Toluene | 20-50 | >20 |
| 6 | 2-Propanol:water (9:1) | 20-51 | >20 |
| 7 | Methanol (MeOH) | 19-49 | >19 |
| 8 | 2-Propanol (IPA) | 19-49 | >19 |
| 9 | Methyl t-butyl ether (MTBE) | 10-20 | >10 |
| 10 | Isopropyl ether (IPE) | 6-11 | >6 |
| 11 | Acetonitrile (MeCN) | 6-10 | >6 |
| 12 | Water | <6 | <6 |

Crystallization experiments were conducted in three modes, including: 1) Temperature-cycled ripening of brexanolone slurries between 40-5° C. for two days (TC) (n=48); 2) Heating slurries to 40° C. followed by hot filtration, then storing of brexanolone solutions at 4° C. for up to two days (RC) (n=48); 3) Evaporation of brexanolone solutions at ambient conditions for up to 7 days (EV) (n=48). A total of 48 solvent systems were involved in the crystal-form screen. The solvents were utilized as neat and binary mixtures to provide a diverse set of polarities, dielectric constants, dipole moments, and hydrogen-bond donor/acceptor attributes. Water-containing solvents with a variety of water activities were also included to probe for the formation of hydrates.

All crystalline outputs from the screen were isolated and analyzed by FT-Raman spectroscopy. The samples were then sorted into groups based on Raman spectral match.

Representative samples from each of the groups were further analyzed by additional techniques (PXRD, DSC, TGA, PLM), as appropriate and as sample quantity permitted. These data were used to support the form assignment which is shown in FIG. 4.

Figure 5:
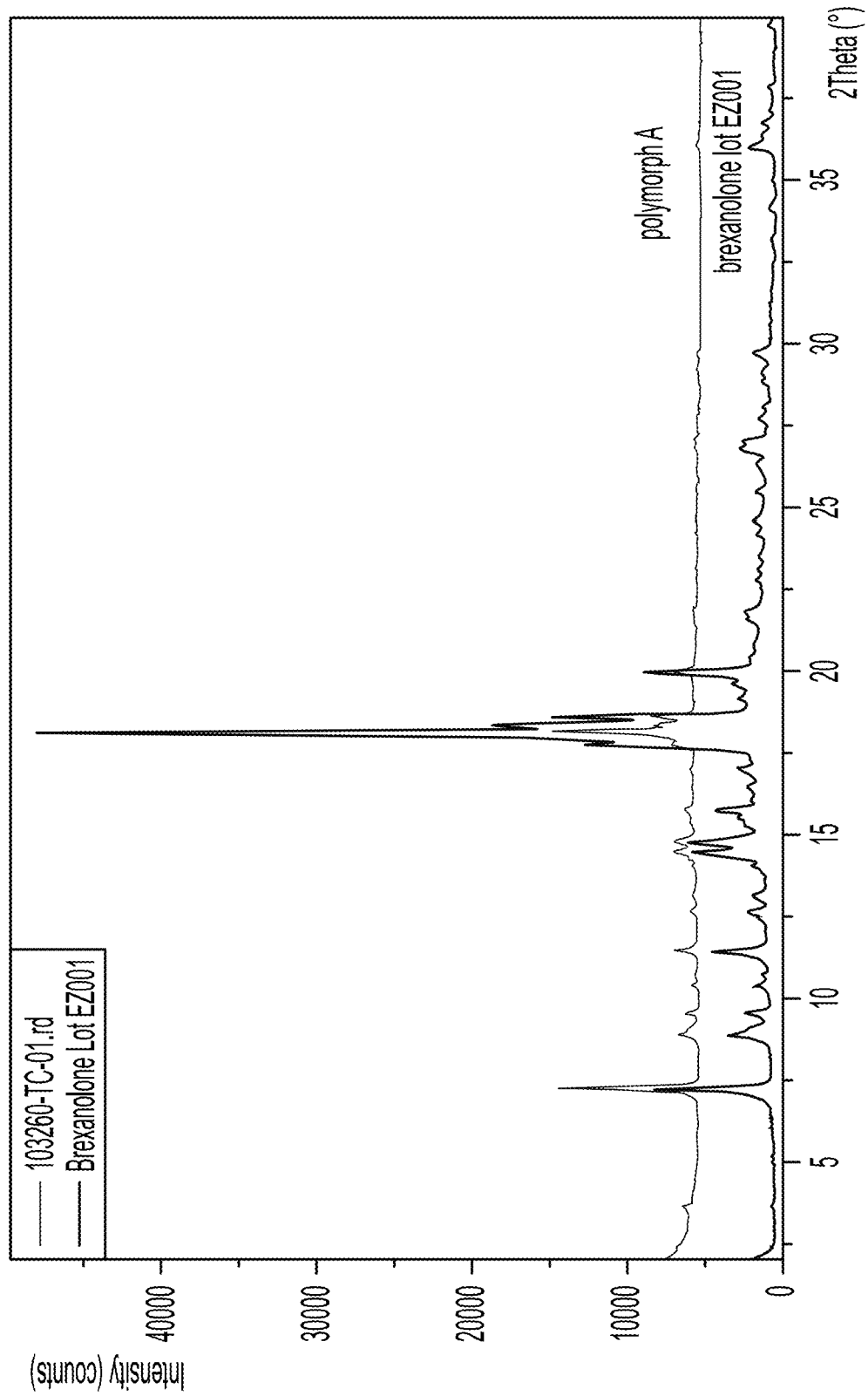
FIG. 5. PXRD pattern overlay of Form A from the input brexanolone and a representative Form A pattern from the screen.

As shown in FIG. 4, 27 crystalline solids were obtained from TC, 14 crystalline solids from RC, and 28 crystalline solids from EV crystallization modes for a total of 69 crystalline solids (shaded). FIG. 5 shows a PXRD pattern overlay of the input brexanolone with a representative Form A pattern from the screen. Polymorph of brexanolone, Form A, was observed in 68 of 69 samples that produced solids. The description of Form A is exemplified by Batch 103260-TC-01. The DSC onset for the melting/decomposition of Lot 103260-TC-01 was 174° C. (ΔH=127 J/g). The TGA % weight loss was <0.1% prior to the melt/decomposition event. Form A is a non-solvated form. The characterization data for Form A along with PXRD peak list are provided in Table 2.

TABLE 2

Ten most intense PXRD peak list of Form A (Batch 103260-TC-01)

| Position [° 2Theta]* | d-spacing [Å] | Relative Intensity [%] |
|---|---|---|
| 18.15 | 4.9 | 100 |
| 7.25 | 12.2 | 91 |
| 18.32 | 4.8 | 40 |
| 18.61 | 4.8 | 31 |
| 17.77 | 5.0 | 19 |
| 14.78 | 6.0 | 18 |
| 19.99 | 4.4 | 18 |
| 14.50 | 6.1 | 16 |
| 11.46 | 7.7 | 16 |
| 8.88 | 10.0 | 14 |

*Data collected with copper K-alpha radiation. K-alpha II mathematically stripped from data prior to peak determination based on copper K-alpha I radiation (1.540598 Å).

Instruments and Methods

FT-Raman Spectroscopy. Raman spectra were collected with a Nicolet NXR9650 or NXR 960 spectrometer (Thermo Electron) equipped with 1064 nm Nd:YVO$_4$ excitation laser, InGaAs and liquid-N2 cooled Ge detectors, and a Micro-Stage. All spectra were acquired at 4 cm$^{-1}$ resolution, 64 to 256 scans, using a neutral density filter and Happ-Genzel apodization function and 2-level zero-filling.

Polarized-light Microscopy (PLM). The photomicrographs were collected using Olympus BX60 polarized-light microscope equipped with Olympus DP70 camera.

Powder X-Ray Diffraction (PXRD). PXRD diffractograms were acquired on PANalytical X'Pert Pro diffractometer using Ni-filtered Cu Kα (45 kV/40 mA) radiation and a step size of 0.02° 2θ and X'celerator™ RTMS (Real Time Multi-Strip) detector. Configuration on the incidental beam side: fixed divergence slit (0.25°), 0.04 rad Soller slits, anti-scatter slit (0.25°), and 10 mm beam mask. Configuration on the diffracted beam side: fixed divergence slit (0.25°) and 0.04 rad Soller slit. Samples were mounted flat on zero-background Si wafers and covered with Kapton film to comply with safety policies.

Powder X-Ray Diffraction (PXRD) Bruker. PXRD diffractograms were acquired on a Bruker D8 Advance system (SN:2631) using Cu Kα (40 kV/40 mA) radiation and a step size of 0.017° 2θ and LynxEye detector. Configuration on the incidental beam side: fixed divergence slit (0.2 mm), 4 mm Soller slits, beam knife. Configuration on the diffracted beam side: anti-scatter slit (8 mm) and 2.5 deg. Soller slit. Samples were mounted flat on zero-background Si wafers.

Differential Scanning calorimetry (DSC). DSC was conducted with a TA Instruments Q100 differential scanning calorimeter equipped with an autosampler and a refrigerated cooling system under 40 mL/min N$_2$ purge. DSC thermograms were obtained at 15° C./min in crimped Al pans. Unless noted otherwise.

Thermogravimetric Analysis (TGA). TGA thermograms were obtained with a TA Instruments Q500 thermogravimetric analyzer under 40 mL/min N$_2$ purge at 15° C./min in Pt or Al pans. Unless noted otherwise.

Example 8: Unit Dose of Injectable Brexanolone Pharmaceutical Composition

A first unit dose of injectable brexanolone composition was packaged as 100 mg/mL injectable solution in a 1 mL via.

A second unit dose of injectable brexanolone composition was packaged as 200 mg/mL injectable solution in a 1 mL via.

A third unit dose of injectable brexanolone composition was packaged as 300 mg/mL injectable solution in a 1 mL via.

A fourth unit dose of injectable brexanolone composition was packaged as 350 mg/mL injectable solution in a 1 mL via.

A fifth unit dose of injectable brexanolone composition was packaged as 400 mg/mL injectable solution in a 1 mL via.

A sixth unit dose of injectable brexanolone composition was packaged as 500 mg/mL injectable solution in a 1 mL via.

A seventh unit dose of injectable brexanolone composition was packaged as 550 mg/mL injectable solution in a 1 mL via.

An eighth unit dose of injectable brexanolone composition was packaged as 600 mg/mL injectable solution in a 1 mL via.

Numbered Embodiments of the Disclosure

Other subject matter contemplated by the present disclosure is set out in the following numbered embodiments:

1. A pharmaceutical composition comprising a pharmaceutically effective amount of a neuroactive steroid, wherein said neuroactive steroid is a positive modulator of gamma-aminobutyric acid type A (GABA$_A$) receptor; and wherein said neuroactive steroid reaches a maximum plasma concentration ($C_{max}$) in about 30 minutes to 6 hours and maintains a plasma concentration of more than about 5% of said $C_{max}$ for at least about 5 days, after a single dose of said pharmaceutical composition by intramuscular or subcutaneous injection.
2. The pharmaceutical composition of embodiment 1, wherein said single dose is about 0.5-50 mg per kilogram of body weight.
3. The pharmaceutical composition of embodiment 2, wherein said single dose is in a range of from about 1 to 8 mg per kilogram of body weight.
4. The pharmaceutical composition of embodiment 2, wherein said single dose is in a range of from about 2 to 6 mg per kilogram of body weight.

5. The pharmaceutical composition of embodiment 2, wherein said single dose is in a range of from about 3 to 5 mg per kilogram of body weight.
6. The pharmaceutical composition of any one of embodiments 1-5, wherein said single dose is about 50 mg to 800 mg per unit dose.
7. The pharmaceutical composition of embodiment 6, wherein said single dose is in a range of from about 50 mg to about 450 mg per unit dose.
8. The pharmaceutical composition of any one of embodiments 1-7, wherein said pharmaceutical composition has a neuroactive steroid concentration of at least about 100 mg/mL.
9. The pharmaceutical composition of embodiment 8, wherein said neuroactive steroid concentration is in a range of from about 100 mg/mL to about 800 mg/mL.
10. The pharmaceutical composition of any one of embodiments 1-7, wherein said neuroactive steroid reaches said $C_{max}$ in about 30 minutes to 1 hour, 1 to 2 hours, 2 to 4 hours, or 4 to 6 hours.
11. The pharmaceutical composition of embodiment 10, wherein said neuroactive steroid reaches said $C_{max}$ in about 1 to 2 hours.
12. The pharmaceutical composition of any one of embodiments 1-11, wherein said neuroactive steroid maintains a plasma concentration of more than about 10%, 15%, 20%, 25%, or 30% of said $C_{max}$ for at least about 10, 20, 30, 40, 50, or 60 days.
13. The pharmaceutical composition of embodiment 12, wherein said neuroactive steroid maintains a plasma concentration of more than about 15% of said $C_{max}$ for at least about 30 days.
14. The pharmaceutical composition of any one of embodiments 1-13, wherein said $C_{max}$ is more than 10 ng/mL.
15. The pharmaceutical composition of embodiment 5, wherein said single dose is in a range of from 3 to about 5 mg per kilogram of body weight, and wherein said neuroactive steroid maintains a plasma concentration of more than about 10 ng/mL for at least about 5 days.
16. The pharmaceutical composition of embodiment 15, wherein said neuroactive steroid maintains a plasma concentration of more than 10, 20, 25, 30, 40, 50, 60, 70, 80, 90, 100 ng/mL for at least about 10, 20, 30, 40, 50, or 60 days.
17. The pharmaceutical composition of any one of embodiments 15-16, wherein said neuroactive steroid maintains a plasma concentration of more than 20 ng/mL for at least about 30 days.
18. The pharmaceutical composition of any one of embodiments 1-15, wherein said pharmaceutical composition releases less than about 5%-50% of said neuroactive steroid within about 1 hour of said single dose of said pharmaceutical composition by intramuscular or subcutaneous injection.
19. The pharmaceutical composition of any one of embodiments 1-18, wherein said pharmaceutical composition has a relative bioavailability of about 2%-50% at 24 hours after said single dose by intramuscular or subcutaneous injection, in comparison to the same dose by intravenous administration.
20. The pharmaceutical composition of any one of embodiments 1-19, wherein said pharmaceutical composition comprises a population of particles comprising said neuroactive steroid, wherein said particles have an average particle size of about 0.2-15 μm.
21. The pharmaceutical composition of embodiment 20, wherein said particles have an average particle size of about 1.5-15 μm.
22. The pharmaceutical composition of embodiment 21, wherein said particles have an average particle size of about 3-5 μm.
23. The pharmaceutical composition of embodiment 20, wherein said particles have an average particle size of about 0.2-1.5 μm.
24. The pharmaceutical composition of embodiment 23, wherein said particles have an average particle size of about 0.5-0.9 μm.
25. The pharmaceutical composition of any one of embodiments 20-24, wherein at least 50%, 60%, 70%, 80%, or 90% by weight of said particles have a particle size of about 0.2-15 μm.
26. The pharmaceutical composition of any one of embodiments 20-25, wherein about 0.01%-50% by weight of said particles have an average particle size of about 1.5-15 μm and about 50% to 99.99% by weight of said particles have an average particle size of about 0.2-1.5 μm.
27. The pharmaceutical composition of any one of embodiments 1-26, wherein said neuroactive steroid comprises tetrahydrodeoxycorticosterone (THDOC), androstane, androstane 3α-androstanediol, cholestane cholesterol, pregnane, eltanolone, brexanolone, ganaxolone, zuranolone, or any combination thereof
28. The pharmaceutical composition of embodiment 27, wherein said neuroactive steroid is brexanolone.
29. The pharmaceutical composition of any one of embodiments 1-28, wherein said pharmaceutical composition is substantially free of cyclodextrins.
30. The pharmaceutical composition of embodiment 29, wherein said pharmaceutical composition is substantially free of sulfobutyl ether β-cyclodextrin.
31. The pharmaceutical composition of any one of embodiments 1-30, further comprising one or more pharmaceutically acceptable excipients.
32. The pharmaceutical composition of embodiment 31, wherein said one or more pharmaceutically acceptable excipients comprise a binder, lubricant, glidant, disintegrant, diluent, coloring agent, surfactant, emulsifier, filler, carrier, isotonicfier, dispersing agent, viscosity modifier, resuspending agent, buffer, or any combination thereof.
33. The pharmaceutical composition of embodiment 31 or 32, wherein said one or more pharmaceutically acceptable excipients comprise acacia, animal oil, benzyl alcohol, benzyl benzoate, calcium stearate, carbomer, cetostearyl alcohol, cetyl alcohol, cholesterol, cyclodextrins, dextrose, diethanolamine, emulsifying wax, ethylene glycol palmitostearate, glycerin, glycerin monostearate, glycerol stearate, glyceryl monooleate, glyceryl monostearate, hydrous, histidine, hydrochloric acid, hydroxypropyl cellulose, hydroxypropyl-β-cyclodextrin (HPBCD), hypromellose (hydroxypropyl methylcellulose (HPMC)), lanolin, lanolin alcohols, lecithin, medium-chain triglycerides, metallic soaps, methylcellulose, mineral oil, monobasic sodium phosphate, monoethanolamine, oleic acid, polyethylene glycol, polyoxyethylene-polyoxypropylene copolymer (poloxamer), polyoxyethylene alkyl ethers, polyoxyethylene castor oil, polyoxyethylene castor oil derivatives, polyoxyethylene sorbitan fatty acid esters, polyoxyethylene stearates, polysorbate, polyoxyethylene (20) sorbitan monolaurate (Tween 20, Polysorbate 20), polyoxyethylene (20) sorbitan monooleate (Tween 80, Polysorbate 80), povidone, propylene glycol alginate, saline, sodium chloride, sodium citrate, sodium citrate dihydrate, sodium hydroxide, sodium lauryl sulfate, sodium phosphate monobasic, sodium phosphate dibasic, sorbitan esters, stearic acid, stearyl alcohol, sunflower oil, tragacanth, triethanolamine, vegetable oil, water, xanthan gum, or any combination thereof.

34. The pharmaceutical composition of any one of embodiments 1-33, comprising a brexanolone polymorph Form A, characterized by having at least three of the following peaks in an X-ray Powder Diffraction (XRPD) diffractogram, at 7.25, 8.88, 11.46, 14.50, 14.78, 17.77, 18.15, 18.32, 18.61, and 19.99±0.1° 2θ.

35. The pharmaceutical composition of any one of embodiments 1-33, wherein said pharmaceutical composition is a liquid suspension for intramuscular or subcutaneous injection.

36. The pharmaceutical composition of embodiment 35, wherein the liquid suspension comprises the brexanolone polymorph Form A.

37. The pharmaceutical composition of any one of embodiments 34-36, wherein the brexanolone polymorph Form A has a chemical purity of greater than 90%.

38. The pharmaceutical composition of any one of embodiments 34-37, wherein the brexanolone polymorph Form A has a melting point of about 170-180° C.

39. The pharmaceutical composition of embodiment 38, wherein the brexanolone polymorph Form A has a melting point of about 174° C.

40. The pharmaceutical composition of any one of embodiments 34-39, wherein the brexanolone polymorph Form A has the following peaks in an X-ray Powder Diffraction (XRPD) diffractogram, at 7.25, 8.88, 11.46, 14.50, 14.78, 17.77, 18.15, 18.32, 18.61, and 19.99±0.1° 2θ.

41. The pharmaceutical composition of any one of embodiments 34-40, wherein the brexanolone polymorph Form A is crystalized from one or more solvents selected from the group consisting of dichloromethane (DCM), tetrahydrofuran (THF), ethyl acetate (EtOAc), dimethyl sulfoxide (DMSO), toluene, 2-propanol:water (9:1), methanol (MeOH), 2-propanol (IPA), methyl t-butyl ether (MTBE), isopropyl ether (IPE), and water.

42. A method of treating a disease in a subject in need thereof, comprising: administering said pharmaceutical composition of any one of embodiments 1-41 to said subject by intramuscular or subcutaneous injection.

43. A method of treating a disease in a subject in need thereof, comprising: administering a pharmaceutical composition comprising a pharmaceutically effective amount of a neuroactive steroid to said subject by intramuscular or subcutaneous injection with a single dose in a range of from 0.5 to 10 mg per kilogram of body weight, wherein said neuroactive steroid is a positive modulator of gamma-aminobutyric acid type A (GABAA) receptor; and wherein said neuroactive steroid reaches a maximum plasma concentration (Cmax) in about 30 minutes to 6 hours and maintains a plasma concentration of more than about 5% of said Cmax for at least about 5 days, after said intramuscular or subcutaneous injection.

44. The method of any one of embodiments 42-43, wherein said disease is selected from the group consisting of anxiety, mood disorder, massive depression disorder, postpartum disorder, Alzheimer disease, Parkinson disease, epilepsy, focal onset seizures, PCDH19 pediatric epilepsy, pediatric genetic epilepsies, CDKL5 Deficiency Disorder (CDD), catamenial epilepsy, infantile spasms, Fragile X syndrome, depression, postpartum depression, and premenstrual syndrome.

45. The method of embodiment 44, wherein said disease is postpartum depression.

46. The method of embodiment 45, wherein said subject has prior history of depression.

47. The method of embodiment 45 or 46, wherein said subject has prior history of postpartum depression.

48. The method of any one of embodiments 42-47, wherein said administering is by a single intramuscular or subcutaneous injection.

49. The method of any one of embodiments 42-47, wherein said pharmaceutical composition is administered to said subject within a time period in a range of from 1 second to about 180 minutes.

50. The method of embodiment 49, wherein said pharmaceutical composition is administered to said subject within a time period in a range of from 1 second to about 30 minutes.

51. The method of any one of embodiments 43-50, wherein said pharmaceutical composition is the pharmaceutical composition of any one of embodiments 1-41.

52. Use of a composition comprising a neuroactive steroid for manufacturing a medicament for treating a disease, wherein said composition is the pharmaceutical composition in any one of embodiments 1-41.

53. Composition comprising a neuroactive steroid for use in a method for the treatment of a disease, wherein said neuroactive steroid is a positive modulator of gamma-aminobutyric acid type A (GABAA) receptor; and wherein said neuroactive steroid reaches a maximum plasma concentration (Cmax) in about 30 minutes to 6 hours and maintains a plasma concentration of more than about 5% of said Cmax for at least about 5 days, after a single dose of said neuroactive steroid by intramuscular or subcutaneous injection.

54. Composition according to embodiment 53, wherein said composition is the pharmaceutical composition of any one of embodiments 1-41.

55. Composition according to embodiment 53, wherein said method is the method of any one of embodiments 42-51.

56. A process for producing the pharmaceutical composition of any one of embodiments 1-41, comprising:
a) mixing a composition comprising said neuroactive steroid with one or more pharmaceutically acceptable excipients; and
b) milling said composition to produce a population of particles of said pharmaceutical composition.

57. A process for producing the pharmaceutical composition of any one of embodiments 1-41, comprising:
a) milling a composition comprising said neuroactive steroid to produce a population of particles; and
b) mixing said composition with one or more pharmaceutically acceptable excipients to produce said pharmaceutical composition.

58. A process for producing the pharmaceutical composition of any one of embodiments 34-40, comprising: crystalizing the brexanolone polymorph Form A from one or more solvents selected from the group consisting of dichloromethane (DCM), tetrahydrofuran (THF), ethyl acetate (EtOAc), dimethyl sulfoxide (DMSO), toluene, 2-propanol:water (9:1), methanol (MeOH), 2-propanol (IPA), methyl t-butyl ether (MTBE), isopropyl ether (IPE), and water.

59. The process of embodiment 58, further comprising:
a) mixing the brexanolone polymorph Form A with one or more pharmaceutically acceptable excipients to form a composition; and
b) milling said composition to produce a population of particles of said pharmaceutical composition.

60. The process of embodiment 58, further comprising:
a) milling a composition comprising the brexanolone polymorph Form A to produce a population of particles; and
b) mixing said composition with one or more pharmaceutically acceptable excipients to produce said pharmaceutical composition.

61. The process of any one of embodiments 56-60, wherein the pharmaceutical composition is a liquid suspension for intramuscular or subcutaneous injection.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

What is claimed is:

1. A pharmaceutical composition comprising brexanolone,
wherein said brexanolone is brexanolone polymorph Form A, characterized by having at least three peaks selected from the group consisting of 7.25±0.1°2θ, 8.88±0.1° 2θ, 11.46±0.1 °2θ, 14.50±0.1 °2θ, 14.78±0.1 °2θ, 17.77±0.1° 2θ, 18.15±0.1 °2θ, 18.32±0.1 °2θ, 18.61±0.1° 2θ, and 19.99±0.1° 2θ in an X-ray Powder Diffraction (XRPD) diffractogram; and
wherein a single dose of said pharmaceutical composition by intramuscular or subcutaneous injection provides a maximum plasma concentration ($C_{max}$) of brexanolone in about 30 minutes to about 6 hours and maintains a plasma concentration of brexanolone of more than about 5% of said $C_{max}$ for at least about 5 days, after the injection.

2. The pharmaceutical composition of claim 1, wherein said single dose comprises about 0.5 mg to about 50 mg of brexanolone per kilogram of body weight.

3. The pharmaceutical composition of claim 2, wherein said single dose comprises about 1 mg to about 8 mg of brexanolone per kilogram of body weight.

4. The pharmaceutical composition of claim 1, wherein said single dose comprises about 50 mg to about 800 mg of brexanolone per unit dose.

5. The pharmaceutical composition of claim 1, wherein the concentration of said brexanolone in the pharmaceutical composition is (a) in a range of from about 100 mg/mL to about 800 mg/mL or (b) about 300 mg/mL.

6. The pharmaceutical composition of claim 1, wherein said single dose of said pharmaceutical composition by intramuscular or subcutaneous injection provides a $C_{max}$ of brexanolone in about 30 minutes to about 300 minutes after the injection.

7. The pharmaceutical composition of claim 1, wherein said single dose of said pharmaceutical composition by intramuscular or subcutaneous injection maintains a plasma concentration of brexanolone of more than about 10% of said $C_{max}$ for at least about 10 days after the injection.

8. The pharmaceutical composition of claim 1, wherein said single dose of said pharmaceutical composition by intramuscular or subcutaneous injection provides a $C_{max}$ of more than 10 ng/ml.

9. The pharmaceutical composition of claim 1, wherein said single dose of said pharmaceutical composition comprises about 3 mg to about 5 mg of brexanolone per kilogram of body weight, wherein said single dose maintains a plasma concentration of brexanolone of more than about 10 ng/mL for at least about 5 days after the injection.

10. The pharmaceutical composition of claim 9, wherein said single dose of said pharmaceutical composition by intramuscular or subcutaneous injection maintains a plasma concentration of brexanolone of more than about 10 ng/ml for at least about 10 days after the injection.

11. The pharmaceutical composition of claim 1, wherein said pharmaceutical composition releases less than about 5% to about 50% of said brexanolone within about 1 hour of said single dose of said pharmaceutical composition by intramuscular or subcutaneous injection.

12. The pharmaceutical composition of claim 1, wherein said pharmaceutical composition provides a relative bioavailability of the brexanolone of about 2% to about 50% at 24 hours after said single dose by intramuscular or subcutaneous injection, in comparison to the same dose by intravenous administration.

13. The pharmaceutical composition of claim 1, wherein said pharmaceutical composition comprises a population of particles comprising said brexanolone, wherein said particles have a mean (D50) particle size of about 0.2 μm to about 15 μm.

14. The pharmaceutical composition of claim 13, wherein said particles have D50 particle size of about 1.2 μm to about 6 μm.

15. The pharmaceutical composition of claim 1, wherein said pharmaceutical composition is substantially free of cyclodextrins.

16. The pharmaceutical composition of claim 15, wherein said pharmaceutical composition is substantially free of sulfobutyl ether β-cyclodextrin.

17. The pharmaceutical composition of claim 1, further comprising one or more pharmaceutically acceptable excipients.

18. The pharmaceutical composition of claim 17, wherein said one or more pharmaceutically acceptable excipients comprise a binder, lubricant, glidant, disintegrant, diluent, coloring agent, surfactant, emulsifier, filler, carrier, isotonicifier, dispersing agent, viscosity modifier, resuspending agent, buffer, or any combination thereof.

19. The pharmaceutical composition of claim 17, wherein said one or more pharmaceutically acceptable excipients comprise acacia, animal oil, benzyl alcohol, benzyl benzoate, calcium stearate, carbomer, cetostearyl alcohol, cetyl alcohol, cholesterol, dextrose, diethanolamine, emulsifying wax, ethylene glycol palmitostearate, glycerin, glycerin monostearate, glycerol stearate, glyceryl monooleate, glyceryl monostearate, hydrous, histidine, hydrochloric acid, hydroxypropyl cellulose, hypromellose (hydroxypropyl methylcellulose (HPMC)), lanolin, lanolin alcohols, lecithin, medium-chain triglycerides, metallic soaps, methylcellulose, mineral oil, monobasic sodium phosphate, monoethanolamine, oleic acid, polyethylene glycol, polyoxyethylene-polyoxypropylene copolymer (poloxamer), polyoxyethylene alkyl ethers, polyoxyethylene castor oil, polyoxyethylene castor oil derivatives, polyoxyethylene sorbitan fatty acid esters, polyoxyethylene stearates, polysorbate, polyoxyethylene (20) sorbitan monolaurate (Tween 20, Polysorbate 20), polyoxyethylene (20) sorbitan monooleate (Tween 80, Polysorbate 80), povidone, propylene glycol alginate, saline, sodium chloride, sodium citrate, sodium citrate dihydrate, sodium hydroxide, sodium lauryl sulfate, sodium phosphate monobasic, sodium phosphate dibasic, sorbitan esters, stearic acid, stearyl alcohol, sunflower oil, tragacanth, triethanolamine, vegetable oil, water, xanthan gum, or any combination thereof.

20. The pharmaceutical composition of claim 1, wherein said pharmaceutical composition is a liquid suspension for intramuscular or subcutaneous injection.

21. The pharmaceutical composition of claim 1, wherein the brexanolone polymorph Form A has a chemical purity of greater than 90%.

22. The pharmaceutical composition of claim 1, wherein the brexanolone polymorph Form A has a melting point of about 170-180° C.

23. The pharmaceutical composition of claim 1, wherein the brexanolone polymorph Form A is characterized by having the following peaks in an X-ray Powder Diffraction (XRPD) diffractogram: 7.25±0.1, 8.88±0.1, 11.46±0.1, 14.50±0.1, 14.78±0.1, 17.77±0.1, 18.15±0.1, 18.32±0.1, 18.61±0.1, and 19.99±0.1° 2θ.

24. A method of treating a disease in a subject in need thereof, comprising administering to said subject by intramuscular or subcutaneous injection the pharmaceutical composition of claim 1.

25. The method of claim 24, wherein the pharmaceutical composition is administered to said subject by a single dose comprising 0.5 mg to 10 mg of brexanolone per kilogram of body weight.

26. The method of claim 24, wherein said disease is selected from the group consisting of anxiety, mood disorder, postpartum disorder, Alzheimer's disease, Parkinson's disease, epilepsy, CDKL5 Deficiency Disorder (CDD), Fragile X syndrome, depression, and premenstrual syndrome.

27. The method of claim 24, wherein said disease is postpartum depression.

28. The method of claim 27, wherein said subject has prior history of depression.

29. The method of claim 27, wherein said subject has prior history of postpartum depression.

30. The method of claim 24, wherein said administering is by a single intramuscular or subcutaneous injection.

31. The method of claim 24, wherein said pharmaceutical composition is administered to said subject within a time period in a range of from 1 second to about 180 minutes.

32. A process for producing the pharmaceutical composition of claim 1, comprising:
   a) mixing said brexanolone with one or more pharmaceutically acceptable excipients to form a mixture; and
   b) milling said mixture to produce a population of particles of said pharmaceutical composition.

33. A process for producing the pharmaceutical composition of claim 1, comprising:
   a) milling brexanolone to produce a population of particles; and
   b) mixing said particles with one or more pharmaceutically acceptable excipients to produce said pharmaceutical composition.

34. A process for producing the pharmaceutical composition of claim 1, comprising: crystalizing the brexanolone polymorph Form A from one or more solvents selected from the group consisting of dichloromethane (DCM), tetrahydrofuran (THF), ethyl acetate (EtOAc), dimethyl sulfoxide (DMSO), toluene, 2-propanol: water (9:1), methanol (MeOH), 2-propanol (IPA), methyl t-butyl ether (MTBE), isopropyl ether (IPE), and water.

35. The method of claim 26, wherein said depression is postpartum depression or massive depression disorder.

36. The method of claim 26, wherein said epilepsy comprises focal onset seizures, PCDH19 pediatric epilepsy, catamenial epilepsy, infantile spasms, or pediatric genetic epilepsies.

37. The method of claim 24, wherein said administering is by two or more intramuscular or subcutaneous injections.

* * * * *